United States Patent [19]

Mochida et al.

[11] 4,237,269

[45] Dec. 2, 1980

[54] DERIVATIVES OF FORTIMICIN A

[75] Inventors: Kenichi Mochida, Hiratsuka; Moriyuki Sato; Shigeo Yoshiie, both of Machida; Yasuki Mori, Kawasaki, all of Japan

[73] Assignee: Abbott Laboratories, North Chicago, Ill.

[21] Appl. No.: 971,435

[22] Filed: Dec. 20, 1978

[30] Foreign Application Priority Data

Dec. 21, 1977 [JP] Japan ................... 52/153000

[51] Int. Cl.$^3$ ............... A61K 31/71; C07H 15/22
[52] U.S. Cl. ............... 536/17 R; 424/180; 536/4

[58] Field of Search ............... 536/4, 17 R

[56] References Cited

U.S. PATENT DOCUMENTS

| | | | |
|---|---|---|---|
| 3,931,400 | 1/1976 | Nara et al. | 424/118 |
| 3,976,768 | 8/1976 | Nara et al. | 424/118 |
| 4,124,756 | 11/1978 | Martin et al. | 536/17 |

*Primary Examiner*—Johnnie R. Brown
*Attorney, Agent, or Firm*—Fitzpatrick, Cella, Harper & Scinto

[57] ABSTRACT

Semisynthetic antibacterial compounds are produced by chemically modifying the antibacterial compound fortimicin A.

3 Claims, No Drawings

DERIVATIVES OF FORTIMICIN A

BACKGROUND OF THE INVENTION

The present invention relates to novel derivatives of fortimicin A, the acid addition salts thereof.

Fortimicins (A, B and C) are compounds belonging to pseudodisaccharide antibiotics containing 1,4-diaminocyclitol. The physical properties and antibacterial activities of these compounds, the processes for producing them by using microorganisms, and processes for separation and purification thereof from culture liquors, etc. are described in detail in U.S. Pat. Nos. 3,931,400, 3,976,768 and 4,048,015.

The planar structural formulae of the fortimicins, are illustrated in said United States Patents and their structural formulae showing absolute coordination are described in the specification of Japanese Published Unexamined Patent Application No. 50140/78.

Fortimicins (A, B and C) all have antibacterial activity, but the antibacterial activity of fortimicin B is not as good as the other factors; and fortimicin A and fortimicin C are slightly unstable under strongly alkaline conditions. Therefore, compounds having more distinguished properties are in demand.

As a result of various studies, it has been found that certain 4-N-substituted derivatives of fortimicin B have enhanced antibacterial activity and good stability under alkaline conditions (Japanese Published Unexamined Patent Application No. 50140/78).

Moreover, it has now been found that certain 2'-N-substituted derivatives of fortimicin A have an excellent antibacterial activity and further that the derivatives have a strong antibacterial activity against the strains resistant to fortimicin A.

SUMMARY OF THE INVENTION

The present invention relates to 2'-N-substituted derivatives of fortimicin A, represented by the general formula (I):

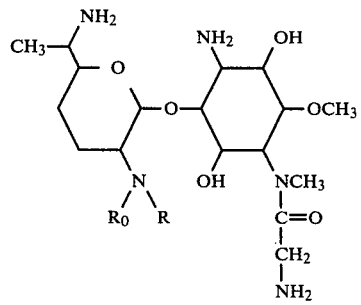

[wherein $R_0$ represents a hydrogen atom or lower alkyl group and R represents a group represented by

or $-CHR_{11}R_{12}$ wherein $R_1$ is an alkyl group, aminoalkyl group, hydroxyalkyl group, carbamoylaminoalkyl group, N-alkylaminoalkyl group, aminohydroxyalkyl group or N-alkylaminohydroxyalkyl group and $R_{11}$ and $R_{12}$ may be the same or different and are a hydrogen atom, alkyl group, aminoalkyl group, hydroxyalkyl group, carbamoylaminoalkyl group, N-alkylaminoalkyl group, aminohydroxyalkyl group, arylalkyl group, N-alkylaminohydroxyalkyl group or aryloxyalkyl group or $R_{11}$ and $R_{12}$ form a cyclohexyl group].

Included in the composition of matter aspect of the invention are the non-toxic acid addition salts of the compounds of the above general formula.

DETAILED DESCRIPTION

Compounds of the present invention are 2'-N-substituted derivatives of fortimicin A, represented by the general formula (I):

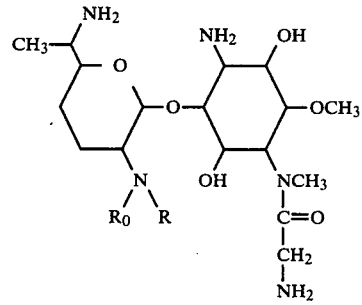

[wherein $R_0$ represents a hydrogen atom or lower alkyl group having 1 to 4 carbon atoms and R represents a group represented by

or $-CHR_{11}R_{12}$ wherein $R_1$ is an alkyl group having 1 to 8 carbon atoms, aminoalkyl group having 2 to 8 carbon atoms, hydroxyalkyl group 1 to 5 carbon atoms, carbamoylaminoalkyl group having 2 to 9 carbon atoms, N-alkylaminoalkyl group having 2 to 12 carbon atoms, aminohydroxyalkyl group having 2 to 8 carbon atoms or N-alkylaminohydroxyalkyl group having 2 to 8 carbon atoms and $R_{11}$ and $R_{12}$ may be the same or different and are a hydrogen atom, alkyl group having 1 to 8 carbon atoms, aminoalkyl group having 1 to 8 carbon atoms, hydroxyalkyl group having 1 to 5 carbon atoms, carbamoylaminoalkyl group having 2 to 9 carbon atoms, N-alkylaminoalkyl group having 2 to 12 carbon atoms, aminohydroxyalkyl group having 2 to 8 carbon atoms, arylalkyl group having 7 to 12 carbon atoms, N-alkylaminohydroxyalkyl group having 2 to 8 carbon atoms or aryloxyalkyl group having 7 to 12 carbon atoms or $R_{11}$ and $R_{12}$ form a cyclohexyl group] and the pharmaceutically acceptable acid addition salts thereof.

The compounds of the present invention and their properties and Rf values in a thin layer chromatography are illustrated in Table 1. For comparison, the data on fortimicin A are also given in Table 1. In a thin layer chromatography, silica gel plate (DC Fertigplatten Kieselgel 60 $F_{254}$ produced by E. Merck & Co., Inc.) is used and development is carried out using lower layer of methanol:chloroform:28% aqueous ammonia=1:1:1 (by volume). Coloring reaction is carried out with ninhydrin.

The nuclear magnetic resonance spectrum and mass spectrum of these compounds are shown in the examples.

TABLE 1

| No. | Compound | $R_0$ | R | Specific rotation of sulfate | Rf |
|---|---|---|---|---|---|
| 1 | fortimicin A | H | H | $[\alpha]_D^{25} = +26.0$ (C = 0.2,H$_2$O) | 0.61 |
| 2 | 2'-N-glycolyl fortimicin A | H | COCH$_2$OH | $[\alpha]_D^{21} = +110.0$ (C = 0.2,H$_2$O) | 0.66 |
| 3 | 2'-N-[(R,S)-3-amino-2-hydroxy-propionyl] fortimicin A | H | COCH(OH)—CH$_2$—NH$_2$ | $[\alpha]_D^{21} = +90.5$ (C = 0.2,H$_2$O) | 0.56, 0.51 |
| 4 | 2'-N-[(S)-4-amino-2-hydroxy-butyryl] fortimicin A | H | CO—CH(OH)—CH$_2$—CH$_2$—NH$_2$ | $[\alpha]_D^{21} = +78.0$ (C = 0.2,H$_2$O) | 0.42 |
| 5 | 2'-N-methyl fortimicin A | H | CH$_3$ | $[\alpha]_D^{23} = +78.5$ (C = 0.2,H$_2$O) | 0.69 |
| 6 | 2'-N-ethyl fortimicin A | H | CH$_2$—CH$_3$ | $[\alpha]_D^{23} = +70.0$ (C = 0.2,H$_2$O) | 0.75 |
| 7 | 2'-N-n-propyl fortimicin A | H | CH$_2$—CH$_2$—CH$_3$ | $[\alpha]_D^{23} = +74.5$ (C = 0.2,H$_2$O) | 0.75 |
| 8 | 2'-N-i-propyl fortimicin A | H | CH(CH$_3$)$_2$ | $[\alpha]_D^{23} = +67.0$ (C = 0.2,H$_2$O) | 0.78 |
| 9 | 2'-N-n-butyl fortimicin A | H | CH$_2$—CH$_2$—CH$_2$—CH$_3$ | $[\alpha]_D^{23} = +73.5$ (C = 0.2,H$_2$O) | 0.80 |
| 10 | 2'-N-i-butyl fortimicin A | H | CH$_2$—CH(CH$_3$)$_2$ | $[\alpha]_D^{22.5} = +71.0$ (C = 0.2,H$_2$O) | 0.80 |
| 11 | 2'-N-sec-butyl fortimicin A | H | CH(CH$_3$)CH$_2$CH$_3$ | $[\alpha]_D^{22.5} = +61.5$ (C = 0.2,H$_2$O) | 0.80 |
| 12 | 2'-N-cyclohexyl fortimicin A | H | cyclohexyl | $[\alpha]_D^{22.5} = +62.0$ (C = 0.2,H$_2$O) | 0.75 |
| 13 | 2'-N-benzyl fortimicin A | H | CH$_2$—C$_6$H$_5$ | $[\alpha]_D^{22.5} = +75.0$ (C = 0.2,H$_2$O) | 0.81 |
| 14 | 2'-N-(3-phenyl-propyl) fortimicin A | H | CH$_2$—CH$_2$—CH$_2$—C$_6$H$_5$ | $[\alpha]_D^{22.5} = +42.5$ (C = 0.2,H$_2$O) | 0.84 |
| 15 | 2'-N-(2-hydroxy-ethyl) fortimicin A | H | CH$_2$—CH$_2$—OH | $[\alpha]_D^{22.5} = +75.5$ (C = 0.2,H$_2$O) | 0.64 |
| 16 | 2'-N-(3-hydroxy-butyl) fortimicin A | H | CH$_2$—CH$_2$—CH(OH)—CH$_3$ | $[\alpha]_D^{22.5} = +55.5$ (C = 0.2,H$_2$O) | 0.69 |
| 17 | 2'-N-[(R,S)-3-amino-2-hydroxy-propyl] fortimicin A | H | CH$_2$—CH(OH)—CH$_2$—NH$_2$ | $[\alpha]_D^{21} = +67.5$ (C = 0.2,H$_2$O) | 0.46 |
| 18 | 2'-N-[(S)-4-amino-2-hydroxy-butyl] fortimicin A | H | CH$_2$—CH(OH)—CH$_2$—CH$_2$—NH$_2$ | $[\alpha]_D^{21} = +63.0$ (C = 0.2,H$_2$O) | 0.38 |
| 19 | 2'-N,N-dimethyl fortimicin A | CH$_3$ | CH$_3$ | $[\alpha]_D^{23} = +65.5$ (C = 0.2,H$_2$O) | 0.78 |

The antibacterial activity of some of the present compounds are determined and the results are shown in Table 2. The determination is carried out according to the Japanese Antibiotic Medicament Standard using a medium having a pH of 7.2. The numerical values indicate minimum inhibitory concentrations (MIC, mcg/ml). The compound numbers correspond to those in Table 1.

The microorganisms used for the determination of antibacterial activity are shown below. The strain numbers in Table 2 correspond to those of the strains indicated below.

| No. | Strain |
|-----|--------|
| ① | *Staphylococcus aureus* 209-P |
| ② | *Staphylococcus aureus* Smith |
| ③ | *Bacillus subtilis* ATCC-6633 |
| ④ | *Escherichia coli* NIHJC-2 |
| ⑤ | *Escherichia coli* 3100 |
| ⑥ | *Klebsiella pneumoniae* #8045 |
| ⑦ | *Shigella sonnei* ATCC-9290 |
| ⑧ | *Providencia* KY 3950 |
| ⑨ | *Pseudomonas aeruginosa* BMH #10 |
| ⑩ | *Escherichia coli* Z-343 *1 |
| ⑪ | *Escherichia coli* KY 8321 *2 |
| ⑫ | *Escherichia coli* KY 8348 *3 |
| ⑬ | *Escherichia coli* 57R/W677 *4 |
| ⑭ | *Pseudomonas aeruginosa* KY 8511 *3 |
| ⑮ | *Pseudomonas aeruginosa* KY 8516 *1 |
| ⑯ | *Providencia* 164 *5 |
| ⑰ | *Klebsiella pneumoniae* 3020Y60 *4 |

*1 produces kanamycin acetyltransferase
*2 produces gentamicin nucleotidyltransferase and neomycin phosphotransferase type II
*3 produces gentamicin acetyltransferase type I
*4 produces gentamicin nucleotidyltransferase
*5 produces gentamicin acetyltransferase type II The strains inactivate antibiotics with the above enzymes produced.

TABLE 2

| Strain No. | Compound No. | | | | | | | | | |
|---|---|---|---|---|---|---|---|---|---|---|
| | 1 | 3 | 4 | 5 | 6 | 8 | 15 | 16 | 17 | 18 |
| 1 | 1.56 | 1.56 | 1.56 | 1.56 | 1.56 | 0.78 | 1.56 | 3.12 | 1.56 | 0.78 |
| 2 | 0.78 | 1.56 | 1.56 | 0.78 | 1.56 | 1.56 | 0.78 | 1.56 | 1.56 | 0.78 |
| 3 | 0.78 | 0.78 | 0.78 | 0.78 | 0.78 | 0.78 | 0.78 | 0.78 | 0.78 | 0.78 |
| 4 | 3.12 | 3.12 | 6.25 | 3.12 | 12.5 | 3.12 | 3.12 | 3.12 | 1.56 | 1.56 |
| 5 | 12.5 | — | 12.5 | 6.25 | 3.12 | 6.25 | 6.25 | 12.5 | — | 6.25 |
| 6 | 1.56 | 1.56 | 1.56 | 1.56 | 1.56 | 3.12 | 1.56 | 3.12 | 0.78 | 1.56 |
| 7 | 12.5 | 25 | 12.5 | 12.5 | 6.25 | 12.5 | 12.5 | 25 | 12.5 | 12.5 |
| 8 | 25 | 25 | 50 | 25 | 12.5 | 25 | 12.5 | 25 | 12.5 | 25 |
| 9 | 0.78 | 1.56 | 1.56 | 1.56 | 1.56 | 0.78 | 0.78 | 1.56 | 1.56 | 0.78 |
| 10 | 1.56 | 1.56 | 3.12 | 3.12 | 3.12 | 3.12 | 1.56 | 1.56 | 1.56 | 1.56 |
| 11 | 12.5 | 12.5 | 12.5 | 12.5 | 12.5 | 12.5 | 6.25 | 12.5 | 12.5 | 12.5 |
| 12 | >100 | 6.25 | 12.5 | 100 | 50 | 12.5 | 12.5 | 6.25 | 6.25 | 12.5 |
| 13 | 6.25 | 6.25 | 6.25 | 12.5 | 6.25 | 6.25 | 3.12 | 6.25 | 6.25 | 6.25 |
| 14 | >100 | >100 | 100 | >100 | >100 | >100 | >100 | >100 | 50 | 50 |
| 15 | 25 | 25 | 50 | 100 | 100 | 100 | 25 | 50 | 12.5 | 25 |
| 16 | 25 | 50 | 25 | 25 | 12.5 | 12.5 | 12.5 | 50 | 50 | 25 |
| 17 | 12.5 | 25 | 12.5 | 12.5 | 12.5 | 25 | 6.25 | 25 | 12.5 | 12.5 |

As apparent from the above results, the compounds of the present invention have a strong antibacterial activity against various microorganisms and therefore are expected to be useful as antibacterial agents and disinfectants. The nontoxic acid addition salts of the present compounds have a broad range of antibacterial spectrum and are also useful as antibacterial agents, etc. The non-toxic acid addition salts of the present invention include the salts of hydrochloric acid, sulfuric acid, hydrobromic acid, amidosulfonic acid, phosphoric acid, maleic acid, acetic acid, citric acid, oxalic acid, succinic acid, benzoic acid, fumaric acid, malic acid, mandelic acid, ascorbic acid, etc.

The process for producing the compounds of the present invention is described below.

The compounds of the present invention are produced according to the steps of Flow Sheets 1–3. The main synthesis routes are (A) a route by which the desired compounds (I) represented by general formula (I) are synthesized from fortimicin B through Steps 1, 2, 5 and 7, (B) a route through Steps 1, 3, 4, 6 and 8, (C) a route through Steps 1, 2, 12, 6 and 8, (D) a route through Steps 1, 2, 5, 9, 10 and 11, (E) a route through Steps 1, 2, 5, 9, 1 and 7, etc.

In the present invention, the compounds represented by general formula (I), general formula (II) . . . are hereinafter referred to as Compounds (I), Compounds (II) . . . respectively.

When Compounds (I) are the compounds wherein $R = -COR_1$, the compounds are mainly synthesized through Steps 1, 2, 5 and 7 (Route A). The compounds can be also synthesized through Steps 1, 2, 5, 9, 1 and 7 (Route E). Route E is an advantageous process on a laboratory scale.

When Compounds (I) are the compounds wherein $R = CH_2R_{13}$ (wherein $R_{13}$ represents an alkyl group, aminoalkyl group, hydroxyalkyl group, carbamoylaminoalkyl group, N-alkylaminoalkyl group, aminohydroxyalkyl group, arylalkyl group, aminohydroxyalkyl group or aryloxyalkyl group), the compounds are synthesized through Steps 1, 3, 4, 6 and 8 (Route B) or through Steps 1, 2, 12, 6 and 8 (Route D).

When Compounds (I) are the compounds wherein $R = CHR'_1R'_2$ (wherein $R'_1$ and $R'_2$ may be the same or different and are an alkyl group, aminoalkyl group, hydroxyalkyl group, arylalkyl group or aryloxyalkyl group, or $R'_1$ and $R'_2$ form a cyclohexyl group), the compounds are synthesized through Steps 1, 2, 5, 9, 10 and 11 (Route E).

In Route E, 1,6'-di[(protected-4-N-(N-protected glycyl)]fortimicin B[Compounds (X)]is used as an intermediate.

In order to synthesize Compounds (X), it is convenient to prepare Compounds (III) having a different aminoprotecting group releasable by a different method at the 2'-position and 1- and 6'-positions respectively. Preferable amino-protecting groups are benzyloxycarbonyl group and tertbutoxycarbonyl group.

Flow Sheet 1
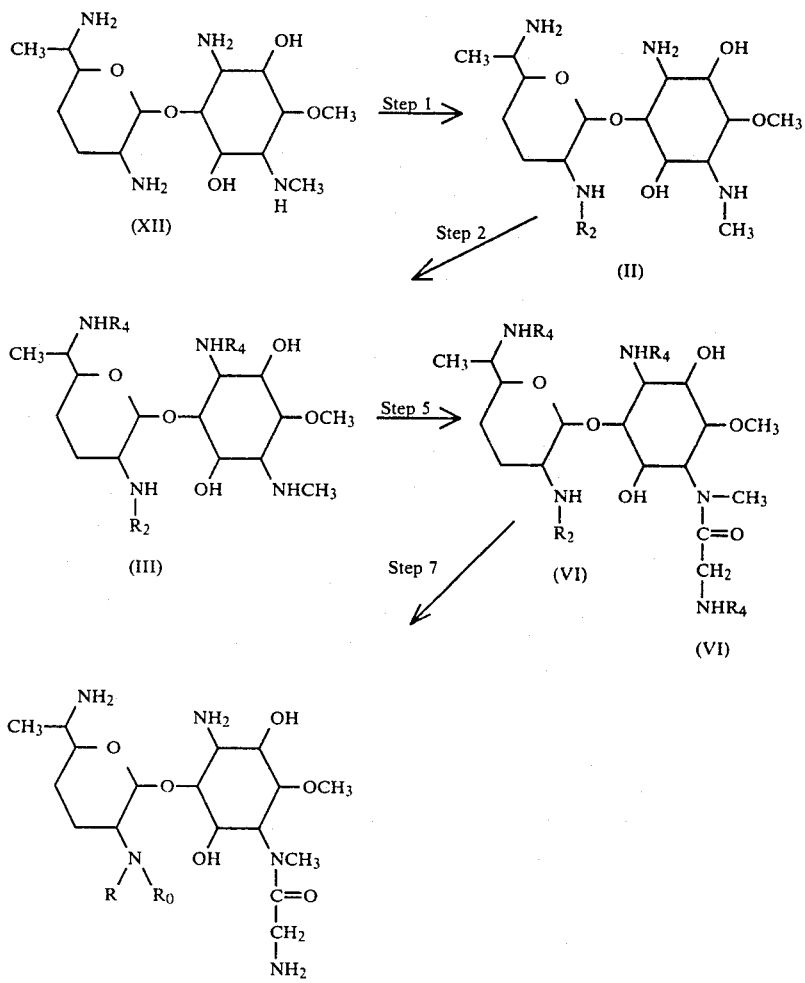
Compounds (I)
Flow Sheet 2
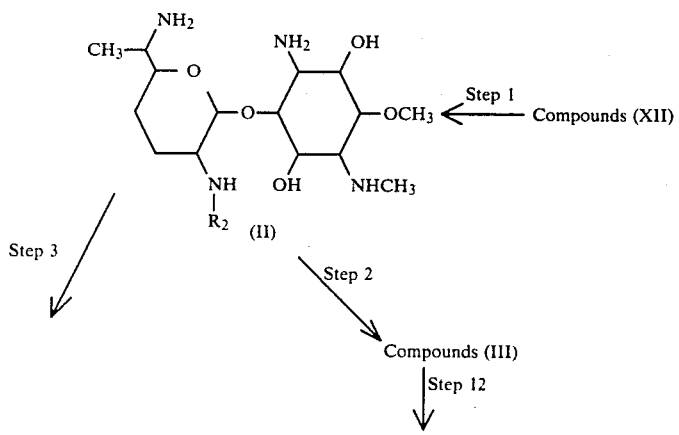

-continued
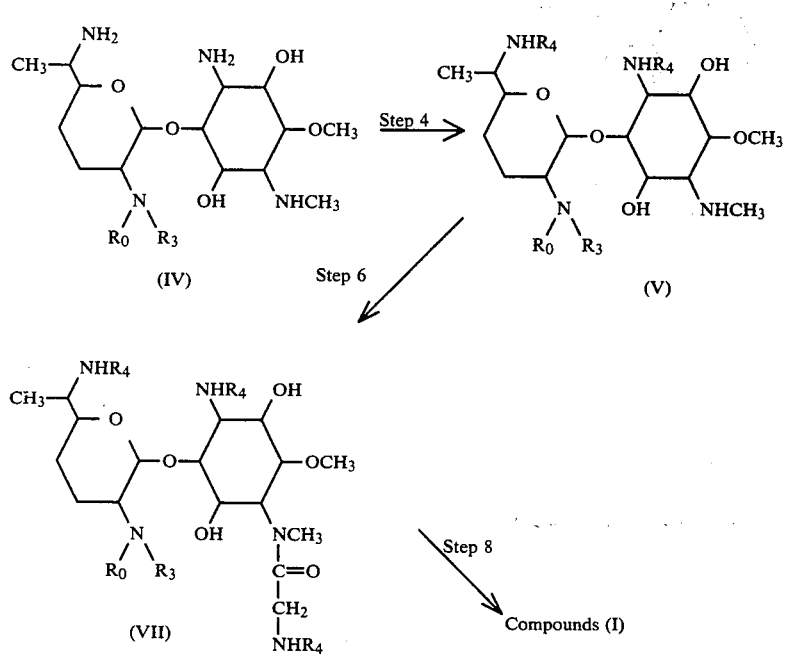
Flow Sheet 3
Compounds (XII) —Step 1→ Compounds (II)
—Step 2→ Compounds (III) —Step 5→
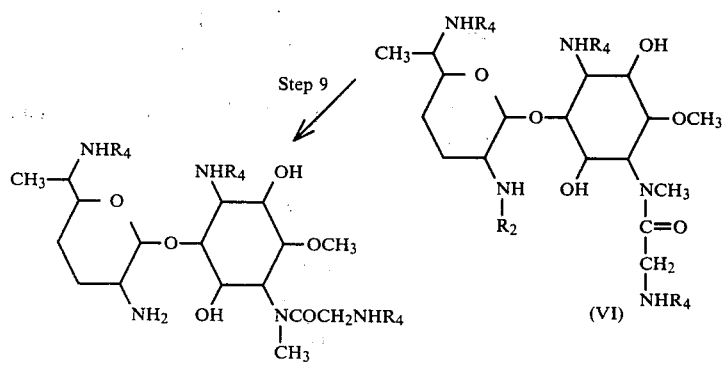

Flow Sheet 3

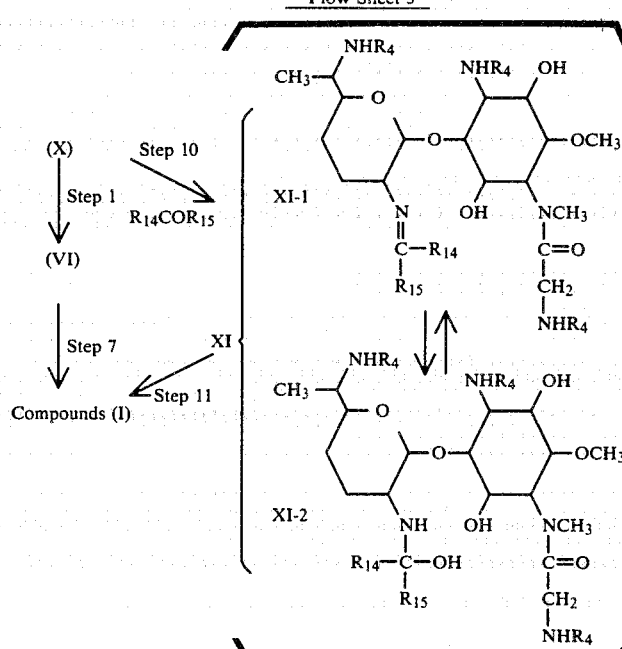

The above steps are explained in detail below.

Step 1.

Synthesis of Compounds (II) represented by general formula (II) from fortimicin B represented by formula (XII)

Compounds (II) are obtained by acylation of fortimicin B using carboxylic acid represented by general formula $R_2OH$ or its derivatives functionally equivalent thereto. $R_2$ represents 1. an acyl group having 2 to 9 carbon atoms, 2. a hydroxyacyl group having 2 to 6 carbon atoms, 3. an alkoxyacyl group having 2 to 6 carbon atoms, 4. a carbamoylaminoacyl group having 3 to 10 carbon atoms, 5. a substituted aminoacyl group having 3 to 17 carbon atoms (the substituent is an amino-protecting group), 6. a substituted aminohydroxyacyl group having 3 to 17 carbon atoms (the substituent is an amino-protecting group), 7. an N-alkylaminoacyl group having 3 to 13 carbon atoms, 8. an N-alkylaminohydroxyacyl group having 3 to 9 carbon atoms or 9. a substituted aminoalkoxycarbonylacyl group having 3 to 17 carbon atoms (the substituent is an aminoprotecting group), an alkoxycarbonyl group having 5 to 10 carbon atoms or an aralkoxycarbonyl group having 8 to 13 carbon atoms.

When $R_2$ is an alkoxycarbonyl group or aralkoxycarbonyl group, an amino-protecting reagent which is usually used in peptide synthesis may be used for the acylation of fortimicin B.

Examples of preferable amino-protecting reagent are shown below.

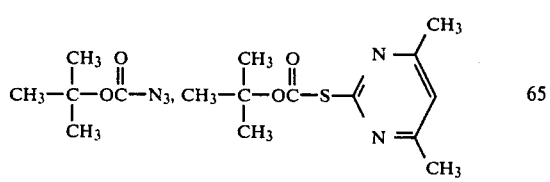

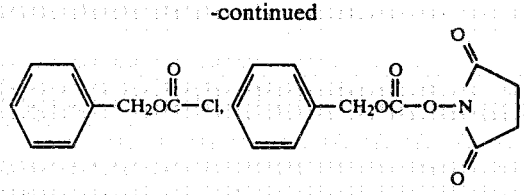

As the carboxylic acid derivatives functionally equivalent to carboxylic acid represented by $R_2OH$, which are used for acylation, carboxylic acid anhydride, active ester, carboxylic acid halides, etc. may be used.

As the active esters, the active esters of said carboxylic acid with one of the compounds represented by

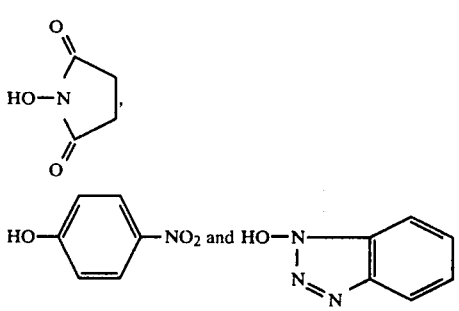

are preferred. The most preferable active ester is an active ester with

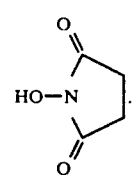

As the reaction solvent, dimethylformamide, tetrahydrofuran, dioxane, methanol, ethanol, acetone, water and mixtures thereof may be used. Among these solvents, methanol and mixture of tetrahydrofuran and water (1:1 by volume) are suitable. The concentration of fortimicin B to be used in the reaction is preferably 5-100 mmoles. The amount of acylating agent is preferably 1-2 moles per mole of fortimicin B. Reaction time is usually 1-24 hours. Reaction temperature is 0°-60° C., preferably 0° C. to room temperature.

Compounds (II) synthesized by the above method are purified and isolated according to the following procedure. The solvent is removed from the reaction mixture by distillation and to the residue is added an equal amount of water to that of the solvent before distillation. The resulting solution is adjusted to pH 5-6 with alkali or acid, and then passed through a column packed with a weakly acidic ion-exchange resin [for example, Amberlite CG-50 ($NH_4^+$ form) (Rohm & Haas Co. Ltd., trade name)]. After washing the column with water, elution is carried out with 0.01-1 N aqueous ammonia. Fractions containing Compounds (II) are combined and the aqueous ammonia is removed by distillation to obtain the desired compound as a white powder. The desired compound is detected by silica gel thin layer chromatography using the lower layer of chloroform:methanol: 14% aqueous ammonia=2:1:1 (by volume) as the developer.

Step 2.

Synthesis of Compounds (III) represented by general formula (III) from Compounds (II) represented by general formula (II)

Compounds (III) are obtained by reacting Compounds (II) with an amino-protecting reagent in an appropriate solvent. Compounds (III) are the compounds wherein the amino groups at the 1- and 6'-positions of Compounds (II) are protected with the amino-protecting group $R_4$.

In this reaction, the amino-protecting reagents represented by the following formulae are preferably used to introduce a t-butoxycarbonyl group.

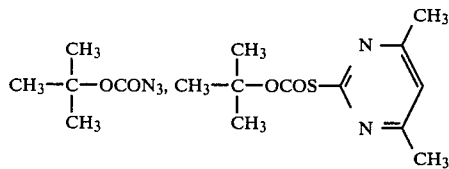

When a benzyloxycarbonyl group is introduced, the amino-protecting reagents represented by the following formulae are preferably used.

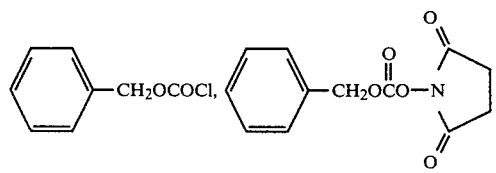

As the reaction solvent, tetrahydrofuran, dioxane, methanol, ethanol and chloroform may be used. Especially, tetrahydrofuran and chloroform are preferred. The concentration of Compounds (II) to be used in the reaction is preferably 5-100 mmoles. The suitable amount of the amino-protecting reagent is 2-3 moles per mole of Compounds (II). Reaction temperature is 0°-60° C. and reaction time is usually 2-48 hours. Compounds (III) synthesized by the above method are isolated and purified according to the following procedure. The solvent is removed from the reaction mixture by distillation. To the resulting residue is added an equal amount of organic solvent such as ethyl acetate, chloroform, etc. to that of the solvent before distillation to extract the soluble part. Then, the extract is subjected to column chromatography using a silica gel [for example, Kieselgel 60 (E. Merck & Co., Inc., trade name)]. Elution is carried out with organic solvent such as chloroform-methanol (99:1–90:10 by volume) and the fractions containing Compounds (III) are combined. The desired compound is detected by thin layer chromatography using chloroform-methanol (9:1 by volume) as the developer. The combined fractions are concentrated to dryness to obtain the desired compound as a white powder. On the other hand, Compounds (III) synthesized as above may be used in a subsequent step as the reaction mixture without isolation.

Step 3.

Synthesis of the compounds represented by general formula (IV) from the compounds represented by general formula (II) Compounds (IV) represented by general formula (IV):

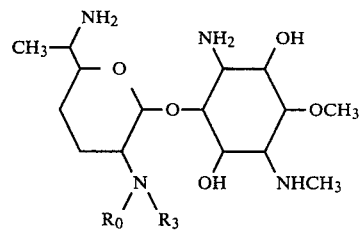

[wherein $R_0$ represents a hydrogen atom or lower alkyl group and $R_3$ represents an alkyl group, hydroxyalkyl group, substituted or unsubstituted aminoalkyl group (the substituent is an amino-protecting group), carbamoylaminoalkyl group, substituted or unsubstituted aminohydroxyalkyl group (the substituent is an amino-protecting group), N-alkylaminoalkyl group or N-alkylaminohydroxyalkyl group] are obtained by reducing Compounds (II) obtained in Step 1 in an appropriate solvent in the presence of a reducing agent at a temperature from room temperature to reflux temperature of the solvent.

Reducing agent is used for converting the carbonyl group of the amide group contained in the substituent $R_2$ in Compounds (II) to a methylene group.

As the solvent, tetrahydrofuran, dioxane and diethyl ether may be used. The concentration of Compounds (II) is preferably 1-100 mmoles. As the reducing agent, usually 10 moles or more of lithium aluminum hydride, diborane, etc. are used in excess of Compounds (II). Reaction time is 3-18 hours. Isolation of Compounds (IV) from the reaction mixture is carried out in the following manner. The excess reducing agent in the reaction mixture is decomposed by adding 10 moles of ethyl acetate, water, etc. per mole of the reducing agent and most of the solvent is distilled away under reduced pressure. The resulting residue is adjusted to pH 5-6 with acid or alkali and 10 times as much water as the residue is added to extract the water-soluble part. Then, the extract is passed through a column packed with a weakly acidic ion-exchange resin [for example, Amberlite CG-50 (NH$_4^+$ form)]. After the column is washed with water, elution is carried out with 0.1-1 N aqueous ammonia and the fractions containing the desired compound are combined. The aqueous ammonia is removed from the combined fractions under reduced pressure to obtain the compounds represented by formula (IV) as a white powder. The desired compound is detected by silica gel thin layer chromatography using lower layer of chloroform-methanol-28% aqueous ammonia (1:1:1 by volume) or lower layer of chloroform-methanol-14% aqueous ammonia (2:1:1 by volume) as the developer.

In Step 3, when there is an amino-protecting group in the substituent R$_3$, the amino-protecting group may be eliminated to facilitate confirmation of the chemical structure. In such a case, a protecting group can be introduced again by increasing the amount of the amino-protecting reagent used in the subsequent protection of the amino groups at the 1- and 6'-positions (Step 4).

Step 4.

Synthesis of Compounds (V) represented by general formula (V) from Compounds (IV) represented by general formula (IV)

Compounds (V) are obtained by reacting Compounds (IV) with an amino-protecting reagent in an appropriate solvent. Compounds (V) are the compounds wherein the amino groups at the 1- and 6'-positions of Compounds (IV) are protected with an amino-protecting group.

The same reaction procedure using the same amino-protecting reagent and the same isolation and purification procedure as in Step 2 are repeated to obtain Compounds (V) as a white powder. The desired compound is detected by thin layer chromatography using chloroform-methanol (9:1 or 19:1 by volume) as the developer.

Step 5.

Synthesis of Compounds (VI) represented by general formula (VI) from the compounds represented by general formula (III)

Compounds (VI) are obtained by subjecting Compounds (III) to condensation reaction with N-protected glycin represented by R$_4$NHCH$_2$CO$_2$H in an appropriate solvent.

AS the N-protecting group (R$_4$) of N-protected glycin, those which are usually used in peptide synthesis can be used, and preferably the same protecting group as in Step 2 is used. Condensation is carried out by condensation method used in peptide synthesis, preferably by active ester method. As the active ester of N-protected glycin in active ester method, esters of N-protected glycin with

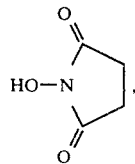

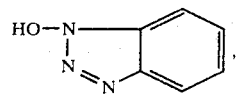

etc. may be used and especially an ester with

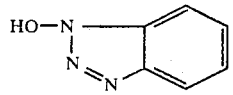

is preferred. The concentration of Compounds (III) is 10-100 mmoles. The reactive derivative of N-protected glycin activated at its carboxyl group is used in an amount of more than 1 mole per mole of Compounds (III). For example, in case of active ester, 1-3 moles of ester is preferably used per mole of Compounds (III). As the solvent, dimethylformamide, tetrahydrofuran, dioxane and chloroform may be used. Reaction is carried out at a temperature of $-10°$ C. to room temperature for 15-20 hours.

Compounds (VI) formed in the reaction mixture by the above reaction are usually used in a subsequent step without isolation. Isolation may be carried out by column chromatography similar to that in Step 2, if desired. The desired compound is detected by silica gel thin layer chromatography using chloroform-methanol (19:1 by volume) as the developer.

Step 6.

Compounds (VII) represented by general formula (VII) are obtained by treating Compounds (V) represented by general formula (V) as the starting material in the same manner as in Step 5.

Step 7.

Synthesis of Compounds (I) represented by general formula (I) from Compounds (VI) represented by general formula (VI)

Compounds (I) are obtained by eliminating the amino-protecting group R$_4$ in Compounds (VI) by a known method.

For example, when the amino-protecting group in Compounds (VI) is a benzyloxycarbonyl group, Compounds (VI) are subjected to catalytic reduction by passing hydrogen gas in the presence of metal catalyst and acid at room temperature and at atmospheric pressure, whereby the amino-protecting group is eliminated. As the solvent, methanol, tetrahydrofuran, dioxane, water and mixtures thereof may be used. As the metal catalyst, palladium carbon, platinum, etc. are used usually in an amount of 1-10 wt% to Compounds (VI). As the acid, hydrochloric acid, sulfuric acid, acetic acid, etc. may be used. The concentration of Compounds (VI) is usually 0.01-1 mole/l. Reaction time is generally 2-18 hours.

Compounds (I) represented by general formula (I) are obtained as an acid addition salt thereof by filtering the reaction mixture and evaporating the resulting filtrate to dryness.

Purification is carried out in the following manner.

The acid addition salt obtained as above is dissolved in a small amount of water. The aqueous solution is passed through a column packed with a weakly acidic ion-exchange resin such as Amberlite CG-50 (NH$_4^+$ form) to adsorb the product on the resin. After the column is washed with 5-10 times as much water as the resin, elution is carried out with 0.1-1 N aqueous ammonia and the active fractions are combined. The solvent is removed therefrom by distillation to obtain the desired compound as a white powder.

The desired compound is detected by silica gel thin layer chromatography using lower layer of chloroform-methanol-28% aqueous ammonia (1:1:1 by volume) as the developer.

Further, when the amino-protecting group in Compounds (VI) is a t-butoxycarbonyl group, the amino-protecting group is eliminated by treating Compounds (VI) with an acid in an appropriate solvent. As the solvent, nonaqueous solvents such as dichloromethane, chloroform, ethyl acetate, etc. may be used. As the acid, hydrochloric acid, trifluoroacetic acid, etc. may be used in an amount of 20-100 moles per mole of Compounds (VI). The concentration of Compounds (VI) is usually 0.1-10 moles/l. Reaction is carried out at a temperature of 0° C. to room temperature for 30 minutes to 8 hours.

Compounds (I) formed in the reaction mixture by the above reaction are obtained as an acid addition salt thereof by evaporating the reaction mixture to dryness. Purification is carried out in the same manner as in the case of a benzyloxycarbonyl group.

Step 8.

Synthesis of Compounds (I) represented by general formula (I) from Compounds (VII) represented by general formula (VII)

Compounds (I) are obtained by eliminating the amino-protecting group $R_4$ in Compounds (VII) by a known method as in Step 7.

Step 9.

Synthesis of the compounds represented by general formula (X) from the compounds represented by general formula (VI)

The compounds represented by general formula (X) are obtained by eliminating the group $R_2$ bonded to the 2'-position of Compounds (VI) by a known method. Elimination is carried out in a similar manner as in Step 7.

In this step, Compounds (VI) wherein $R_2$ at the 2'-position is the amino-protecting group represented by

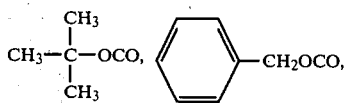

starting material. Further, in this step, Compounds (VI) wherein the amino-protecting groups at the 1- and 6'-positions are different from that at the 2'-position are used as the starting material. For example, the compound wherein $R_2$ at the 2'-position is

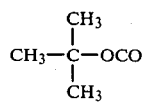

and the amino-protecting group $R_4$ at the 1- and 6'-positions is

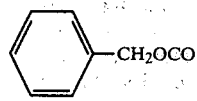

and the compound wherein $R_2$ at the 2'-position is

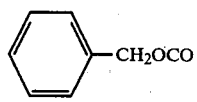

and the amino-protecting group $R_4$ at the 1- and 6'-positions is

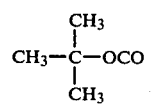

are preferably used.

Step 10.

Synthesis of the compounds represented by general formula (I) from the compounds represented by general formula (XI)

Compounds (XI) represented by general formula (XI) are obtained by reacting Compounds (X) represented by general formula (X) with an aldehyde or ketone represented by general formula $R_{14}COR_{15}$ (wherein $R_{14}$ and $R_{15}$ may be the same or different and are a hydrogen atom, alkyl group, aryl group, aralkyl group, hydroxyalkyl group or N-protected aminoalkyl group, or $R_{14}$ and $R_{15}$ form a cyclohexyl group) in the presence of a reducing agent.

The obtained Compounds (XI) are usually converted to Compounds (I) without isolation.

As the aldehyde used in the reaction, aliphatic aldehyde having 1 to 16 carbon atoms, aromatic aldehyde having 7 to 12 carbon atoms and substituted aliphatic aldehyde having 2 to 6 carbon atoms (the substituent represents a hydroxyl group or an N-protected amino group) may be used. As the ketone, aliphatic ketone having 3 to 10 carbon atoms, aromatic ketone having 8 to 14 carbon atoms, cyclic ketone having 3 to 10 carbon atoms and substituted aliphatic ketone having 3 to 14 carbon atoms (the substituent represents a hydroxyl group or an N-protected amino group) may be used. Sodium boron hydride and sodium cyanoboron hydride may be used as the reducing agent. As the solvent, methanol, ethanol, tetrahydrofuran, dioxane, water and mixtures thereof may be used. Especially, methanol is preferred. The concentration of Compounds (X) to be used in the reaction is 10-100 mmoles.

The aldehyde, ketone and reducing agent are used in an amount of 1-50 moles per mole of Compounds (X). Reaction is carried out at a temperature of 0° C. to room temperature usually for 2-18 hours.

Step 11.

Synthesis of Compounds (I) represented by general formula (I) from Compounds (XI) represented by general formula (XI)

Compounds (I) are obtained by eliminating the amino-protecting group R$_4$ in Compounds (XI) obtained in Step 10 by a known method.

Usually, Compounds (XI) obtained in Step 10 are used as the raw material without isolation.

Reaction and purification are carried out in a similar manner as in Step 7.

For example, when the amino-protecting group in Compounds (XI) is a benzyloxycarbonyl group, the same procedure as in Step 7 is repeated adding metal catalyst after the completion of reaction of Step 10.

When the amino-protecting group in Compounds (XI) is a t-butoxycarbonyl group, the reaction mixture resulting from the reaction of Step 10 is concentrated to dryness under reduced pressure and then treated in the same manner as in Step 7 in the presence of an acid.

Step 12.

Reaction is carried out according to the procedure of Step 3.

Further, Compounds (I) can be synthesized using Compounds (X) as the intermediate as described below.

Compounds (X) are reacted with an amino-protecting reagent in an appropriate solvent as in Step 2. The obtained Compounds (VI) are treated in a similar manner as in Step 7 without or after isolation to eliminate the amino-protecting group, whereby Compounds (I) are obtained.

The practice of the present invention is illustrated by the following examples. The procedures in the examples were performed according to the respective steps as follows.

| Examples | Step |
|---|---|
| Examples 1, 2, 4, 19, 20, 21, 32, 33 | Step 1 |
| Examples 6, 10, 11 | Step 2 |
| Examples 8, 9, 22, 34, 37 | Step 3 |
| Examples 22, 31, 35, 37, 38 | Step 4 |
| Examples 7 | Step 5 |
| Examples 23, 24, 31, 36, 37, 38 | Step 6 |
| Examples 19, 20, 21, 32 | Step 7 |
| Examples 23, 24, 31, 36, 37, 38, | Step 8 |
| Examples 12 | Step 9 |
| Examples 14, 15, 16, 17, 18, 25, 26, 27, 28, 29, 30 | Step 10 |
| Examples 14, 15, 16, 17, 18, 25, 26, 27, 28, 29, 30 | Step 11 |
| Examples 13, 35 | Step 12 |

EXAMPLE 1

Synthesis of 2'-N-t-butoxycarbonyl fortimicin B [the compound represented by general formula (II) wherein R$_2$=(CH$_3$)$_3$COCO]

6.0 g of fortimicin B is dissolved in 300 ml of 50% aqueous tetrahydrofuran. To the solution is added 5.8 g of t-butyl-S-4,6-dimethylpyrimidine-2-ylthiocarbonate (1.4 moles per mole of the starting compound) and the mixture is allowed to stand at room temperature for 18 hours. Then, tetrahydrofuran is removed from the reaction mixture by distillation under reduced pressure. 150 ml of water is added to the resulting aqueous solution and the solution is adjusted to pH 5.5 with 1 N HCl.

The solution is passed through a column (2.5 cm in inside diameter) packed with 200 ml of a weakly acidic cation exchange resin, Amberlite CG-50 (NH$_4$$^+$ form). After the column is washed with 1 l of water, elution is carried out with 0.1 N aqueous ammonia and the eluate is taken in 20 g fractions. Fraction Nos. 22–44 are combined and concentrated under reduced pressure to obtain 2.86 g of a white powder. The powder has the following properties and is identified as 2'-N-butoxycarbonyl fortimicin B. Yield: 37% Rf value in silica gel thin layer chromatography [hereinafter referred to as TLC, plate: Fertigplatten Kieselgel 60 F$_{254}$ produced by E. Merck & Co., Inc. (the same gel is used in TLC hereinafter), developer: lower layer of chloroform:methanol:14% aqueous ammonia=2:1:1 (by volume; the same shall apply hereinafter)]: 0.63 Nuclear magnetic resonance spectrum (in methanol-d$_4$) δ (in ppm) 1.07(3H, d), 1.43(9H, s), 2.41(3H, s), 3.47(3H, s), 4.98(1H, s)

EXAMPLE 2

Synthesis of 2'-N-[(S)-4-benzyloxycarbonylamino-2-hydroxybutryl]fortimicin B [the compound represented by general formula (II) wherein R$_2$=COCH(OH)CH$_2$CH$_2$NHCOOCH$_2$C$_6$H$_5$]

5.0 g of fortimicin B is dissolved in 200 ml of methanol. To the solution is added, in about 500 mg portions, 6.0 g of N-hydroxysuccinimide ester of (S)-4-benzyloxycarbonylamino-2-hydroxybutyric acid, and the mixture is allowed to react at room temperature for 3 hours. After the reaction mixture is concentrated under reduced pressure, 200 ml of water is added thereto and the water-soluble part is extracted. The solution is adjusted to pH 5.5 with 1 N HCl and then passed through a column (2.5 cm in inside diameter) packed with 150 ml of a weakly acidic ion exchange resin, Amberlite CG-50 (NH$_4$$^+$ form). After the column is washed with 600 ml of water, elution is carried out with 0.1 N aqueous ammonia and the eluate is taken in 20 ml fractions. Fraction Nos. 38–64 are combined and concentrated under reduced pressure. The aqueous ammonia is removed therefrom by distillation to obtain 3.4 g of a white powder. The powder has the following properties and is identified as 2'-N-[(S)-4-benzyloxycarbonylamino-2-hydroxybutyryl]fortimicin B. Yield: 40.6%

Rf value in silica gel TLC (developer: lower layer of chloroform:methanol:14% aqueous ammonia=2:1:1): 0.37

Nuclear magnetic resonance spectrum (in methanol-d$_4$) δ (in ppm): 1.04(3H, d), 2.37(3H, s), 3.43(3H, s), 5.03(2H, s), 5.06(1H, d), 7.26(5H, s)

EXAMPLE 3

Synthesis of 2'-N-[(S)-4-amino-2-hydroxybutyryl]fortimicin B [the compound represented by general formula (II) wherein R$_2$=COCH(OH)CH$_2$.CH$_2$.NH$_2$]

For further confirming the chemical structure, 1.4 g of the powder obtained in Example 2 is dissolved in 25 ml of 0.2 N-HCl methanol*. To the solution is added 150 mg of palladium carbon catalyst and reductive hydrogenolysis is carried out by passing hydrogen gas at room temperature and at atmospheric pressure for 3 hours. The catalyst is removed from the reaction mixture by filtration and the obtained filtrate is concentrated. 25 ml of water is added thereto and the resulting solution is adjusted to pH 5.5 with 1 N NaOH. Then, the solution is passed through a column (2 cm in inside diameter) packed with 45 ml of Amberlite CG-50 (NH$_4$$^+$ form). After the column is washed with 500 ml of water, elution is carried out with 0.4 N aqueous ammonia and the eluate is taken in 15 ml fractions. Fraction Nos. 48–70 are combined and the aqueous ammonia is removed therefrom by distillation to obtain 1.0 g of a white powder. The powder has the following properties and is identified as 2'-N-[(S)-4-amino-2-hydroxybutyryl]fortimicin B. Yield: 92.7%

*0.2 N-HCl methanol is prepared by diluting 12 N HCl with methanol. The same shall apply hereinafter.

Rf value in silica gel TLC (developer: lower layer of chloroform:methanol: 28% aqueous ammonia=1:1:1): 0.41

Nuclear magnetic resonance spectrum (in methanol-$d_4$) δ (in ppm): 1.06(3H, s), 1.5–2.05(6H, m), 2.42(3H, s), 2.7–3.2(5H, m), 3.48(3H, s), 5.17(1H, d)

EXAMPLE 4

Synthesis of 2'-N-benzyloxyacetyl fortimicin B [the compound represented by general formula (II) wherein $R_2=COCH_2OCH_2C_6H_5$]

The same procedure as in Example 2 is repeated except that 4.5 g of N-hydroxysuccinimide ester of benzyloxyacetic acid (O-benzylglycolic acid) is used in place of 6.0 g of N-hydroxysuccinimide ester of (S)-4-benzyloxycarbonylamino-2-hydroxybutyric acid. Fraction Nos. 18–25 are combined and concentrated under reduced pressure to obtain 1.68 g of a white powder. The powder has the following properties and is identified as 2'-N-benzyloxyacetyl fortimicin B. Yield: 23.6%

Rf value in silica gel TLC (developer:lower layer of chloroform:methanol:14% aqueous ammonia=2:1:1):0.45

Nuclear magnetic resonance spectrum (in methanol-$d_4$) δ (in ppm): 1.05(3H, d), 2.35(3H, s), 3.45(3H, s), 3.94(4H, s), 5.10(1H, d), 7.35(5H, s)

EXAMPLE 5

Synthesis of 2'-N-glycolyl fortimicin B [the compound represented by general formula (II) wherein $R_2=COCH_2OH$]

For further confirming the chemical structure, 1.2 g of the powder obtained in Example 4 is subjected to hydrogenolysis in the same manner as in Example 3. As the result, 0.95 g of a white powder is obtained. The powder has the following properties and is identified as 2'-N-glycolyl fortimicin B. Yield: 96.7%

Rf value in silica gel TLC (developer: lower layer of chloroform:methanol:28% aqueous ammonia=1:1:1): 0.56

Nuclear magnetic resonance spectrum (in methanol-$d_4$) δ (in ppm): 1.06(3H, d), 1.5–2.0(4H, m), 2.40(3H, s), 3.45(3H, s), 3.94(2H, s), 5.10(1H, d)

EXAMPLE 6

Synthesis of 2'-N-t-butoxycarbonyl-1,6'-di-N-benzyloxycarbonyl fortimicin B [the compound represented by general formula (III) wherein $R_4=COOCH_2C_6H_5$ and $R_2=COOC(CH_3)_3$]

2.0 g of 2'-N-t-butoxycarbonyl fortimicin B obtained in Example 1 is dissolved in 120 ml of methanol. To the solution is added 2.44 g (2.2 moles per mole of the starting compound) of N-benzyloxycarbonyloxysuccinimide and the mixture is allowed to react at room temperature for 3 hours. The methanol is removed from the reaction mixture by distillation under reduced pressure. 120 ml of ethyl acetate is added to the residue and then the solution is washed with 120 ml of water. After the ethyl acetate layer is dried over anhydrous sodium sulfate, the solvent is distilled away under reduced pressure to obtain a crude powder of the desired compound. For purification, the crude powder is dissolved in 10 ml of chloroform and the solution is passed through a column (2.5 cm in inside diameter) packed with 80 g of a silica gel (Kieselgel 60 produced by E. Merck & Co., Inc.; the same gel is used as the silica gel hereinafter). Elution is carried out with chloroform-methanol (24:1) and the eluate is taken in 20 ml fractions. Fraction Nos. 19–60 are combined and the solvent is removed therefrom by distillation to obtain 2.42 g of a white powder. The powder has the following properties and is identified as 2'-N-t-butoxycarbonyl-1,6'-di-N-benzyloxycarbonyl fortimicin B. Yield: 75.7%

Rf value in silica gel TLC (developer: chloroform:methanol=9:1): 0.52

Nuclear magnetic resonance spectrum (in methanol-$d_4$) δ (in ppm): 1.02(3H, d), 1.40(9H, s), 2.37(3H, s), 3.47(3H, s), 5.03(4H, s), 5.31(1H, d), 7.30(10H, s)

EXAMPLE 7

Synthesis of 2'-N-t-butoxycarbonyl-1,6'-di-N-benzyloxycarbonyl-4-N-(N-benzyloxycarbonylglycyl)fortimicin B [the compound represented by general formula (VI) wherein $R_2=(CH_3)_3COCO$ and $R_4=C_6H_5CH_2OCO$]

800 mg of N-benzyloxycarbonylglycin and 540 mg of 1-hydroxybenzotriazole are dissolved in 80 ml of tetrahydrofuran. To the solution is added 890 mg of N,N'-dicyclohexylcarbodiimide, and the mixture is stirred under ice cooling (0°–5° C.) for one hour, whereby [1-hydroxybenzotriazole ester of N-benzyloxycarbonylglycin] is synthesized. The solution is then mixed with 2.40 g of 2'-N-t-butoxycarbonyl-1,6'-di-N-benzyloxycarbonyl fortimicin B obtained in Example 6. The mixture is stirred at room temperature for 18 hours. The precipitated insoluble matters are removed by filtration and the filtrate is concentrated to dryness under reduced pressure to obtain a pale yellowish crude powder of the desired compound. For purification, the obtained residue is dissolved in 10 ml of chloroform and the solution is passed through a column (2 cm in inside diameter) packed with 80 g of a silica gel. Elution is carried out with methanol-chloroform (1:49) and the eluate is taken in 16 ml fractions. Fraction Nos. 11–32 are combined and concentrated to dryness to obtain 2.69 g of a white powder. The powder has the following properties and is identified as 2'-N-t-butoxycarbonyl-1,6'-di-N-benzyloxycarbonyl-4-N-(N-benzyloxycarbonylglycyl) fortimicin B. Yield: 88.5%

Rf value in silica gel TLC (developer: chloroform:methanol=19:1): 0.40

Nuclear magnetic resonance spectrum (in methanol-$d_4$) δ (in ppm): 1.13(3H, d), 1.35(9H, s), 3.07(3H, s), 3.35(3H, s), 4.06(2H, s), 5.03(2H, s), 5.07(4H, s), 7.29(15H, s)

EXAMPLE 8

Synthesis of 2'-N-[(S)-4-amino-2-hydroxybutyl]fortimicin B [the compound represented by general formula (IV) wherein $R_3=CH(OH)CH_2CH_2NH_2$]

1.51 g of 2'-N-[(S)-4-amino-2-hydroxybutyryl] fortimicin B obtained in Example 3 is suspended in 50 ml of tetrahydrofuran and 35 ml of a diborane solution in tetrahydrofuran (1 mole solution of $BH_3$) is added thereto. The mixture is gently refluxed under heating for 2 hours. After the mixture is cooled to room temperature, 6.3 ml of water is added thereto and the mixture is concentrated to dryness. The obtained residue is dissolved in 50 ml of 0.2 N-HCl methanol. The solution is allowed to stand at room temperature for 18 hours and then most of the solvent is distilled away. 50 ml of water is added to the resultant residue and the solution is adjusted to pH 6 with 1 N NaOH. Thereafter, the solution is passed through a column (1.5 cm in inside diameter) packed with 75 ml of Amberlite CG-50 ($NH_4^+$ form). After the column is washed with 600 ml of water, elution is carried out with 0.3 N aqueous ammonia and the eluate is taken in 15 ml fractions. Fraction Nos. 22-72 are combined and the aqueous ammonia is removed therefrom by distillation to obtain 1.27 g of a white powder. The powder has the following properties and is identified as 2'-N-[(S)-4-amino-2-hydroxybutyl]fortimicin B. Yield: 86.5%

Rf value in silica gel TLC
(a) developer: lower layer of chloroform:methanol:28% aqueous ammonia = 1:1:1: 0.48
(b) developer: isopropanol:methanol:28% aqueous ammonia = 2:1:1: 0.41

Mass spectrum (m/e): 435(M+), 417, 400, 387, 361, 332, 272, 235, 230, 207, 181, 155, 142, 126, 112, 105, 86, 70, 57

EXAMPLE 9

Synthesis of 2'-N-methyl fortimicin B [the compound represented by general formula (IV) wherein $R_0=H$ and $R_3=CH_3$]

2.79 g of 2'-N-t-butoxycarbonyl fortimicin B obtained in Example 1 is dissolved in 100 ml of tetrahydrofuran and 2.3 g of lithium aluminum hydride is added thereto. The mixture is gently refluxed under heating for 3 hours. After the mixture is cooled to room temperature, 20 ml of water is added thereto and the excess reducing agent is decomposed. The precipitate is removed by filtration and the filtrate is concentrated. After adjusting the pH of the concentrate to 5.5 with 1 N HCl, 200 ml of water is added to extract the water-soluble part. The resulting aqueous solution is passed through a column (2.5 cm in inside diameter) packed with 150 ml of Amberlite CG-50 ($NH_4^+$ form). After the column is washed with 1 l of water, elution is carried out with 0.2 N aqueous ammonia and the eluate is taken in 20 ml fractions. Fraction Nos. 30-51 are combined and the aqueous ammonia is removed therefrom by distillation under reduced pressure to obtain 1.62 g of a white powder. The powder has the following properties and is identified as 2'-N-methyl fortimicin B. Yield: 71.9%

Rf value in silica gel TLC (developer:lower layer of chloroform:methanol:28% aqueous ammonia = 1:1:1):0.71

Mass spectrum (m/e): 362(M+), 331, 282, 235, 207, 189, 173, 157, 128, 86, 57

EXAMPLE 10

Synthesis of 2'-N-glycolyl-1,6'-di-N-benzyloxycarbonyl fortimicin B [the compound represented by general formula (III) wherein $R_3=COCH_2OH$ and $R_4=COOCH_2C_6H_5$]

1.12 g of 2'-N-glycolyl fortimicin B obtained in the same manner as in Example 5 is dissolved in 40 ml of methanol. To the solution is added 1.51 g (2.2 moles per mole of the starting compound) of N-benzyloxycarbonyloxysuccinimide and the mixture is allowed to react at room temperature for 18 hours. Then, the reaction mixture is concentrated and 40 ml of ethyl acetate is added to the residue to extract the soluble part. After concentration, the ethyl acetate layer is subjected to purification using a column (1.5 cm in inside diameter) packed with 60 g of a silica gel. Elution is carried out with methanol-chloroform (1:16) and the eluate is taken in 20 ml fractions. Fraction Nos. 17-105 are combined and the solvent is removed therefrom by distillation to obtain 1.03 g of a white powder. The powder has the following properties and is identified as 2'-N-glycolyl-1,6'-di-N-benzyloxycarbonyl fortimicin B. Yield: 55.4%

Rf value in silica gel TLC
(a) developer:methanol:chloroform = 1:9:0.14
(b) developer:lower layer of chloroform:methanol:14% aqueous ammonia = 2:1:1:0.67

Nuclear magnetic resonance spectrum (in methanol-$d_4$) δ (in ppm): 1.02(3H, d), 2.40(3H, s), 3.40(3H, s) 3.94(2H, s), 5.01(4H, s), 5.23(1H, d), 7.24(10H, s)

EXAMPLE 11

Synthesis of 2'-N-[(S)-4-benzyloxycarbonylamino-2-hydroxybutyryl]-1,6'-di-N-benzyloxycarbonyl fortimicin B [the compound represented by general formula (III) wherein $R_2=COCH(OH)CH_2CH_2NHCOOCH_2C_6H_5$ and $R_4=COOCH_2C_6H_5$]

2.0 g of 2'-N-[(S)-4-benzyloxycarbonylamino-2-hydroxybutyryl]fortimicin B synthesized in Example 2 is dissolved in 50 ml of methanol. To the solution is added 1.9 g (2.2 moles per mole of the starting compound) of N-benzyloxycarbonyloxysuccinimide and the mixture is stirred at room temperature for 18 hours. Then, the reaction mixture is concentrated and 50 ml of ethyl acetate is added to the residue to extract the soluble part. After concentration, the ethyl acetate layer is passed through a column (2 cm in inside diameter) packed with 90 g of a silica gel. Elution is carried out with methanol-chloroform (1:12) and the eluate is taken in 20 ml fractions. Fraction Nos. 32-85 are combined and the solvent is removed therefrom by distillation to obtain 2.03 g of a white powder. The powder has the following properties and is identified as 2'-N-[(S)-4-benzyloxycarbonylamino-2-hydroxybutyryl]-1,6'-di-N-benzyloxycarbonyl fortimicin B.

Rf value in silica gel TLC (developer:methanol:chloroform = 1:9):0.32

Nuclear magnetic resonance spectrum (in methanol-$d_4$) δ (in ppm): 1.02(3H, d), 2.40(3H, s), 3.42(3H, s) 5.01(6H, s), 5.20(1H, d), 7.20(15H, s)

EXAMPLE 12

Synthesis of 1,6'-di-N-benzyloxycarbonyl-4-N-(N-benzyloxycarbonylglycyl)fortimicin B [the compound represented by general formula (X) wherein $R_4=COOCH_2C_6H_5$]

2.53 g of 2'-N-t-butoxycarbonyl-1,6'-di-N-benzyloxycarbonyl-4-N-(N-benzyloxycarbonylglycyl)fortimicin B obtained in Example 7 is dissolved in 20 ml of chloroform. To the solution is added 10 ml of trifluoroacetic acid (about 20 moles per mole of the starting compound) and the mixture is allowed to react at room temperature for one hour. Then, the reaction mixture is concentrated under reduced pressure and 150 ml of ethyl acetate is added to the residue. The resulting ethyl acetate solution is washed with water and saturated aqueous solution of sodium hydrogencarbonate. After the ethyl acetate layer is dried over anhydrous sodium sulfate, the solvent is removed by distillation under reduced pressure to obtain 1.93 g of a white powder. The powder has the following properties and is identified as 1,6'-di-N-benzyloxycarbonyl-4-N-(N-benzyloxycarbonylglycyl)fortimicin B.

Rf value in silica gel TLC (developer:chloroform:methanol = 9:1):0.18

Nuclear magnetic resonance spectrum (in methanol-d$_4$) δ (in ppm): 1.13(3H, d), 3.07(3H, s), 3.36(3H, s), 4.89(1H, d), 5.05(2H, s), 5.09(4H, s), 7.30(15H, s)

EXAMPLE 13

Synthesis of 2'-N-(2-hydroxyethyl)-1,6'-di-N-benzyloxycarbonyl fortimicin B [the compound represented by general formula (V) wherein $R_3 = CH_2CH_2OH$ and $R_4 = COOCH_2C_6H_5$]

1.0 g of 2'-N-glycolyl-1,6'-di-N-benzyloxycarbonyl fortimicin B obtained in Example 10 is dissolved in 10 ml of tetrahydrofuran. To the solution is added 20 ml of a diborane solution in tetrahydrofuran (1 mole solution of BH$_3$) at room temperature and the mixture is stirred for one hour. Then, 0.6 ml of water is added thereto and the reaction is stopped. The reaction mixture is concentrated to dryness. To the resulting residue is added 30 ml of 0.2 N-HCl methanol and the mixture is allowed to stand at room temperature for 18 hours. After the methanol is removed from the reaction mixture by distillation, 20 ml of water is added to the residue and the pH is adjusted to 10 with 1 N NaOH. 30 ml of ethyl acetate is added to the solution to extract the soluble part and then the ethyl acetate layer is washed with water. After the ethyl acetate layer is dried over anhydrous sodium sulfate, the solvent is removed by distillation to obtain 620 mg of a white powder. The powder has the following properties and is identified as 2'-N-(2-hydroxyethyl)-1,6'-di-N-benzyloxycarbonyl fortimicin B. Yield: 63.3%

Rf value in silica gel TLC (developer:lower layer of chloroform:methanol:14% aqueous ammonia=4:1:1):0.31

Nuclear magnetic resonance spectrum (in methanol-d$_4$) δ (in ppm): 1.02(3H, d), 2.37(3H, s), 3.47(3H, s), 5.03(4H, s), 7.30(10H, s)

EXAMPLE 14

Synthesis of 2'-N,N-dimethyl fortimicin A [the compound represented by general formula (I) wherein $R = R_0 = CH_3$]

800 mg of 1,6'-di-N-benzyloxycarbonyl-4-N-(N-benzyloxycarbonylglycyl)fortimicin B obtained in Example 12 is dissolved in 12 ml of methanol. To the solution are added 0.20 ml of 37% aqueous solution of formaldehyde and 22.4 mg of sodium boron hydride, and the mixture is stirred at room temperature for 4 hours. Then, 1.2 ml of 1 N HCl and 80 mg of 10% palladium carbon catalyst are added to the reaction mixture and reductive hydrogenolysis is carried out by passing hydrogen gas at room temperature and at atmospheric pressure for 3 hours. After the catalyst is removed from the reaction mixture by filtration, the solvent is distilled away and the residue is dissolved in 10 ml of water. The resulting solution is passed through a column (1.2 cm in inside diameter) packed with 30 ml of Amberlite CG-50 (NH$_4^+$ form). After the column is washed with 60 ml of water, elution is carried out with 0.2 N aqueous ammonia and the eluate is taken in 10 ml fractions. Fraction Nos. 9-14 are combined and the aqueous ammonia is removed therefrom by distillation to obtain 310 mg of a white powder. The powder has the following properties and is identified as 2'-N,N-dimethyl fortimicin A. Yield: 71.5%

Rf value in silica gel TLC (developer:lower layer of chloroform:methanol:28% aqueous ammonia=1:1:1):0.78

Nuclear magnetic resonance spectrum (in D$_2$O) δ (in ppm): 1.05(3H, d), 2.36(6H, s), 3.08(3H, s), 3.44(3H, s), 3.52(2H, d), 4.98(1H, d)

Mass spectrum (m/e): 433(M$^+$), 376, 292, 246, 235, 187, 170, 71

Specific rotation (sulfate): $[\alpha]_D^{23} = +65.5°$ (C=0.2, H$_2$O)

EXAMPLE 15

Synthesis of 2'-N-ethyl fortimicin A [the compound represented by general formula (I) wherein $R_0 = H$ and $R = CH_2CH_3$]

The same procedure as in Example 14 is repeated except that 0.07 ml of 81% aqueous solution of acetaldehyde is used in place of 0.20 ml of 37% aqueous solution of formaldehyde. As the result, 210 mg of a white powder is obtained from Fraction Nos. 18-26. The powder has the following properties and is identified as 2'-N-ethyl fortimicin A. Yield: 49%

Rf value in silica gel TLC (developer:lower layer of chloroform:methanol:28% aqueous ammonia=1:1:1):0.75

Nuclear magnetic resonance spectrum (in D$_2$O) δ (in ppm): 1.04(3H, d), 1.08(3H, t), 3.05(3H, s), 3.43(3H, s), 3.51(2H, s), 5.04(1H, d)

Specific rotation (sulfate): $[\alpha]_D^{23} = +70.0°$ (C=0.2, H$_2$O)

Mass spectrum (m/e): 433(M$^+$), 376, 292, 246, 207, 189, 187, 171, 71

EXAMPLE 16

Synthesis of 2'-N-i-propyl fortimicin A [the compound represented by general formula (I) wherein $R_0 = H$ and $R = CH(CH_3)_2$]

800 mg of 1,6'-di-N-benzyloxycarbonyl-4-N-(N-benzyloxycarbonylglycyl)fortimicin B obtained in Example 12 is dissolved in 10 ml of methanol. To the solution are added 4 ml of acetone and 100 mg of sodium boron hydride, and the mixture is stirred at room temperature for 5 hours. Then, the reaction mixture is concentrated under reduced pressure. 20 ml of 0.2 N-HCl methanol and 80 mg of 10% palladium carbon catalyst are added to the resulting residue and reductive hydrogenolysis is carried out by passing hydrogen gas at room temperature and at atmospheric pressure for 3 hours. After the catalyst is removed from the reaction mixture by filtration, the solvent is distilled away and 10 ml of water is added to the residue. The resulting solution is adjusted to pH 5.5 with 1 N NaOH and then passed through a column (1.2 cm in inside diameter) packed with 30 ml of Amberlite CG-50 (NH$_4^+$ form). After the column is washed with 150 ml of water, elution is carried out with 0.2 N aqueous ammonia and the eluate is taken in 10 ml fractions. Fraction Nos. 15-25 are combined and the aqueous ammonia is removed therefrom by distillation to obtain 290 mg of a white powder. The powder has the following properties and is identified as 2'-N-i-propyl fortimicin A. Yield: 65%

Rf value in silica gel TLC (developer:lower layer of chloroform:methanol:28% aqueous ammonia=1:1:1):0.78

Nuclear magnetic resonance spectrum (in D$_2$O) δ (in ppm): 1.02(3H, d), 1.06(6H, d), 3.06(3H, s), 3.44(3H, s), 3.52(2H, s), 5.07(1H, d)

Specific rotation (sulfate): $[\alpha]_D^{23} = +67.0°$ (C=0.2, H$_2$O)

Mass spectrum (m/e): 447(M$^+$), 390, 292, 246, 207, 185, 142, 85, 70

EXAMPLE 17

Synthesis of 2'-N-sec-butyl fortimicin A [the compound represented by general formula (I) wherein $R_0=H$ and $R=CH(CH_3)CH_2CH_3$]

The same procedure as in Example 16 is repeated except that 4 ml of methyl ethyl ketone is used in place of 4 ml of acetone. As the result, 280 mg of a white powder is obtained from Fraction Nos. 13-21. The powder has the following properties and is identified as 2'-N-sec-butyl fortimicin A. Yield: 61%

Rf value in silica gel TLC (developer:lower layer of chloroform:methanol:28% aqueous ammonia=1:1:1):0.80

Nuclear magnetic resonance spectrum (in $D_2O$) δ (in ppm): 0.97(3H, t), 1.03–1.04(6H, d), 3.04(3H, s), 3.42(3H, s), 3.53(2H, s), 5.00(1H, d)

Specific rotation (sulfate): $[\alpha]_D^{22.5}=+61.5°$ (C=0.2,$H_2O$)

Mass spectrum (m/e): 461($M^+$), 404, 246, 235, 207, 199, 198, 99

EXAMPLE 18

Synthesis of 2'-N-cyclohexyl fortimicin A [the compound represented by general formula (I) wherein $R_0=H$ and $R=$ $$-CH\underset{CH_2CH_2}{\overset{CH_2CH_2}{<\phantom{xx}>}}CH_2]$$

The same procedure as in Example 16 is repeated except that 5 ml of cyclohexanone is used in place of 4 ml of acetone. As the result, 310 mg of a white powder is obtained from Fraction Nos. 16-22. The powder has the following properties and is identified as 2'-N-cyclohexyl fortimicin A. Yield: 64%

Rf value in silica gel TLC (developer:lower layer of chloroform:methanol:28% aqueous ammonia=1:1:1):0.75

Nuclear magnetic resonance spectrum (in $D_2O$) δ (in ppm): 1.01(3H, d), 3.03(3H, s), 3.41(3H, s), 3.50(2H, s), 5.0(1H, d)

Specific rotation (sulfate): $[\alpha]_D^{22.5}=+62.0°$ (C=0.2, $H_2O$)

Mass spectrum (m/e): 487 ($M^+$), 456, 430, 381, 368, 350, 312, 235, 207, 142, 125

EXAMPLE 19

Synthesis of 2'-N-[(S)-4-amino-2-hydroxybutyryl]fortimicin A [the compound represented by general formula (I) wherein $R_0=H$ and $R=COCH(OH)CH_2CH_2NH_2(S)$]

250 mg of 1,6'-di-N-benzyloxycarbonyl-4-N-(N-benzyloxycarbonylglycyl)fortimicin B obtained in Example 12 is dissolved in 20 ml of ethyl acetate. To the solution is added 141 mg of (S)-4-benzyloxycarbonylamino-2-hydroxybutyric acid N-hydroxysuccinimide ester, and the mixture is allowed to react at room temperature for 3 hours. Then, the reaction mixture is concentrated. 20 ml of 0.2 N-HCl methanol and 25 mg of palladium carbon catalyst are added to the resulting residue and reductive hydrogenolysis is carried out by passing hydrogen gas at room temperature and at atmospheric pressure for 3 hours. After the catalyst is removed from the reaction mixture by filtration, the filtrate is concentrated and the residue is dissolved in 5 ml of water. The resulting solution is adjusted to pH 5.5 with 1 N NaOH and then passed through a column (1 cm in inside diameter) packed with 20 ml of Amberlite CG-50 ($NH_4^+$ form). After the column is washed with 100 ml of water, elution is carried out with 0.4 N aqueous ammonia and the eluate is taken in 5 ml fractions. Fraction Nos. 38-47 are combined and the aqueous ammonia is removed therefrom by distillation to obtain 186 mg of a white powder. The powder has the following properties and is identified as 2'-N-[(S)-4-amino-2-hydroxybutyryl]fortimicin A. Yield: 84%

Rf value in silica gel TLC (developer: lower layer of chloroform:methanol:28% aqueous ammonia=1:1:1): 0.42

Nuclear magnetic resonance spectrum (in $D_2O$) δ (in ppm): 1.03(3H, d), 3.05(3H, s), 3.43(3H, s), 3.50(2H, s), 4.93(1H, d)

Specific rotation (sulfate): $[\alpha]_D^{21}=+78.0°$ (C=0.2,$H_2O$)

Mass spectrum (m/e): 506($M^+$), 472, 400, 369, 301, 244, 235, 207, 143, 126, 101, 86

EXAMPLE 20

Synthesis of 2'-N-[(S)-4-amino-2-hydroxybutyryl]fortimicin A (another method)

120 mg of N-benzyloxycarbonylglycin and 75 mg of 1-hydroxybenzotriazole are dissolved in 12 ml of tetrahydrofuran. To the solution is added 110 mg of N,N'-dicyclohexylcarbodiimide and the mixture is stirred under ice cooling (0°-5° C.) for one hour. Then, 430 mg of 2'-N-[(S)-4-benzyloxycarbonylamino-2-hydroxybutyryl]-1,6'-di-N-benzyloxycarbonyl fortimicin B obtained in Example 11 is added thereto and the mixture is stirred at room temperature for 18 hours. The precipitated insoluble material is removed by filtration and the filtrate is concentrated. Thereafter, as in Example 19, the resulting residue is dissolved in 0.2 N-HCl methanol and reductive hydrogenolysis is carried out in the presence of palladium carbon catalyst to eliminate the amino-protecting groups. The desired compound formed in the reaction mixture is purified in the same manner as in Example 19 to obtain 166 mg of a white powder. The powder has the same properties as the powder obtained in Example 19 and is identified as 2'-N-[(S)-4-amino-2-hydroxybutyryl]fortimicin A. Yield: 65%

EXAMPLE 21

Synthesis of 2'-N-glycolyl fortimicin A [the compound represented by general formula (I) wherein $R_0=H$ and $R=COCH_2OH$]

The same procedure as in Example 19 is repeated except that 98 mg of N-hydroxysuccinimide ester of benzyloxyacetic acid (O-benzylglycolic acid) is used in place of (S)-4-benzyloxycarbonylamino-2-hydroxybutyric acid N-hydroxysuccinimide ester. Elution is carried out with 0.2 N aqueous ammonia and as the result, 101 mg of a white powder is obtained from Fraction Nos. 7-14. The powder has the following properties and is identified as 2'-N-glycolyl fortimicin A. Yield: 71%

Rf value in silica gel TLC (developer: lower layer of chloroform:methanol:28% aqueous ammonia=1:1:1): 0.66

Nuclear magnetic resonance spectrum (in $D_2O$) δ (in ppm): 1.03(3H, d), 3.04(3H, s), 3.43(3H, s), 3.50(2H, s), 4.10(2H, s), 5.0(1H, d)

Specific rotation (sulfate): $[\alpha]_D^{21} = +110.0°$ (C=0.2, $H_2O$)

EXAMPLE 22

Synthesis of 2'-N-[(S)-4-benzyloxycarbonylamino-2-hydroxybutyl]-1,6'-di-N-benzyloxycarbonyl fortimicin B [the compound represented by general formula (V) wherein $R_3=$

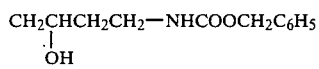

and $R_4=COOCH_2C_6H_5$]

1.2 g (2.0 mmoles) of 2'-N-[(S)-4-benzyloxycarbonylamino-2-hydroxybutyryl]fortimicin B obtained in Example 2 is dissolved in 20 ml of tetrahydrofuran. To the solution is added 20 ml of a solution of diborane in tetrahydrofuran (1 mole solution of $BH_3$) and the mixture is allowed to reat at room temperature for one hour. 0.5 ml of water is added to the reaction mixture and the unreacted diborane is decomposed. After the mixture is concentrated to dryness, 20 ml of 0.2 N-HCl methanol is added to the residue and the mixture is allowed to stand at room temperature for 18 hours. Then, the reaction mixture is concentrated and 20 ml of water is added thereto. The resulting solution is adjusted to pH 10 with 1 N NaOH and then mixed with 40 ml of tetrahydrofuran. To the mixture is added 550 mg of N-benzyloxycarbonyloxysuccinimide and reaction is carried out at room temperature for 3 hours. After the reaction mixture is concentrated, 60 ml of chloroform is added to the residue to extract the soluble part. Then, the chloroform layer is passed through a column (2.5 cm in inside diameter) packed with 80 g of a silica gel to adsorb the reaction product. Elution is carried out with chloroform-methanol (9:1) and the eluate is taken in 20 ml fractions. Fraction Nos. 71-100 are combined and the solvent is removed therefrom by distillation to obtain 720 mg of a white powder. The powder has the following properties and is identified as the above-mentioned compound. Yield: 43.0%

Rf value in silica gel TLC (developer: chloroform:methanol=9:1): 0.16

Nuclear magnetic resonance spectrum (in methanol-$d_4$) δ (in ppm): 1.04(3H, d), 1.1-1.8(6H, m), 2.34(3H, s), 2.4-3.1(6H, m), 3.44(3H, s), 5.08(6H, s), 5.14 (1H, d), 7.34(15H, s)

EXAMPLE 23

Synthesis of 2'-N-[(S)-4-amino-2-hydroxybutyl]fortimicin A [the compound represented by general formula (I) wherein $R_0=H$ and $R=CH_2CH(OH)CH_2CH_2NH_2$]

90 mg of N-benzyloxycarbonylglycin and 58 mg of 1 N-hydroxybenzotriazole are dissolved in 8 ml of tetrahydrofuran. To the solution is added 90 mg of N,N-dicyclohexylcarbodiimide and the mixture is stirred under ice cooling (0°-5° C.) for one hour, whereby an active ester of N-benzyloxycarbonylglycin is synthesized. Then, 300 mg of 2'-N-[(S)-4-benzyloxycarbonylamino-2-hydroxybutyl]-1,6'-di-N-benzyloxycarbonyl fortimicin B obtained in Example 22 is added thereto and reaction is carried out at room temperature for 18 hours. The precipitated insoluble material is removed from the reaction mixture by filtration and the filtrate is concentrated. To the resulting residue are added 10 ml of 0.2 N-HCl methanol and 30 mg of palladium carbon catalyst, and reductive hydrogenolysis is carried out by passing hydrogen gas at room temperature and at atmospheric pressure for 5 hours. After the catalyst is removed by filtration, the filtrate is concentrated and 10 ml of water is added to the residue. The resulting solution is adjusted to pH 5.5 with 1 N NaOH and then passed through a column (1.2 cm in inside diameter) packed with 30 ml of Amberlite CG-50 ($NH_4^+$ form). After the column is washed with 150 ml of water, elution is carried out with 0.5 N aqueous ammonia and the eluate is taken in 10 ml fractions. Fraction Nos. 33-43 are combined and the aqueous ammonia is removed therefrom by distillation to obtain 112 mg of a white powder. The powder has the following properties and is identified as 2'-N-[(S)-4-amino-2-hydroxybutyl]fortimicin A. Yield: 61%

Rf value in silica gel TLC (developer: lower layer of chloroform:28% aqueous ammonia:methanol=1:1:1): 0.38

Nuclear magnetic resonance spectrum (in $D_2O$) δ (in ppm): 1.04(3H, d), 3.05(3H, s), 3.44(3H, s), 3.52(2H, s), 5.04(1H, d)

Specific rotation (sulfate): $[\alpha]_D^{21} = +63.0°$ (C=0.2, $H_2O$)

EXAMPLE 24

Synthesis of 2'-N-(2-hydroxyethyl)fortimicin A [the compound represented by general formula (I) wherein $R_0=H$ and $R=CH_2CH_2OH$]

The same procedure as in Example 23 is repeated except that 240 mg of 2'-N-(2-hydroxyethyl)-1,6'-di-N-benzyloxycarbonyl fortimicin B obtained in Example 13 is used in place of 2'-N-[(S)-4-benzyloxycarbonylamino-2-hydroxybutyl]-1,6'-di-N-benzyloxycarbonyl fortimicin B. To the 4-N-position of the obtained compound is introduced N-benzyloxycarbonylglycin and then the amino-protecting groups at the 4-N-, 1- and 6'-positions are eliminated, whereby the desired compound is formed. The product is treated in the same manner as in Example 23 and elution is carried out with 0.15 N aqueous ammonia. As the result, 92 mg of a white powder is obtained from Fraction Nos. 9-11. The powder has the following properties and is identified as 2'-N-(2-hydroxyethyl) fortimicin A. Yield: 58%

Rf value in silica gel TLC (developer: lower layer of chloroform:methanol:28% aqueous ammonia=1:1:1): 0.64

Nuclear magnetic resonance spectrum (in $D_2O$) δ (in ppm): 1.05(3H, d), 3.04(3H, s), 3.43(3H, s), 3.52(2H, s), 5.01(1H, d)

Specific rotation (sulfate): $[\alpha]_D^{22.5} = +75.5°$ (C=0.2, $H_2O$)

EXAMPLE 25

Synthesis of 2'-N-n-propyl fortimicin A [the compound represented by general formula (I) wherein $R_0=H$ and $R=CH_2-CH_2-CH_3$]

800 mg (1.0 mmole) of 1,6'-di-N-benzyloxycarbonyl-4-N-(N-benzyloxycarbonylglycyl) fortimicin B obtained in Example 12 is dissolved in 12 ml of methanol. To the solution are added 230 mg (4.0 mmoles) of propionaldehyde and 75 mg (2 mmoles) of sodium boron hydride, and the mixture is allowed to react at room temperature for 3 hours. The reaction mixture is concentrated and 15 ml of 0.2 N-HCl methanol is added to the residue. Then, hydrogenolysis and purification are carried out in the same manner as in Example 14. Fraction Nos. 26-38 are combined and the aqueous ammonia is removed therefrom by distillation to obtain 270 mg of a white powder. The powder has the following properties and is identified as 2'-N-n-propyl fortimicin A.
Yield: 61%

Rf value in silica gel TLC (developer: lower layer of chloroform:methanol:28% aqueous ammonia=1:1:1): 0.78

Nulear magnetic resonance spectrum (in $D_2O$) δ (in ppm): 0.97(3H, t), 1.05(3H, d), 3.04(3H, s), 3.43(3H, s), 3.53(2H, s), 5.0(H, d)

Specific rotation (sulfate): $[\alpha]_D^{23} = +74.5°$ (C=0.2, $H_2O$)

Mass spectrum (m/e): 447(M+), 390, 292, 264, 246, 235, 207, 185, 184, 85

EXAMPLES 26-30

The same procedure as in Example 25 is repeated except that 4 mmoles of the aldehyde shown below is respectively used in place of 4 mmoles of propionaldehyde.

| Example No. | Used aldehyde | Weight |
|---|---|---|
| 26 | normalbutylaldehyde | 290 mg |
| 27 | isobutylaldehyde | 290 mg |
| 28 | aldol | 350 mg |
| 29 | benzaldehyde | 420 mg |
| 30 | β-phenylpropionaldehyde | 540 mg |

The yields and the properties of the obtained white powders are as follows. The powders are respectively identified as the desired compounds.

(EXAMPLE 26)

Synthesis of 2'-N-n-butyl fortimicin A [the compound represented by general formula (I) wherein $R_0$=H and R=$CH_2CH_2CH_2CH_3$]
Yield: 290 mg 63%

Rf value in silica gel TLC (developer: lower layer of chloroform:28% aqueous ammonia:methanol=1:1:1): 0.80

Nuclear magnetic resonance spectrum (in $D_2O$) δ (in ppm): 0.98(3H, t), 1.04(3H, d), 3.05(3H, s), 3.43(3H, s), 3.52(2H, s), 5.03(1H, d)

Specific rotation (sulfate): $[\alpha]_D^{23} = +73.5°$ (C=0.2, $H_2O$)

Mass spectrum (m/e): 461(M+), 404, 246, 235, 215, 207, 199, 198, 99

(EXAMPLE 27)

Synthesis of 2'-N-isobutyl fortimicin A [the compound represented by general formula (I) wherein $R_0$=H and R=$CH_2CH(CH_3)_2$]
Yield: 310 mg 68%

Rf value in silica gel TLC (developer: lower layer of chloroform:methanol:28% aqueous ammonia=1:1:1): 0.80

Nuclear magnetic resonance spectrum (in $D_2O$) δ (in ppm): 0.85(6H, d), 1.04(3H, d), 3.04(3H, s), 3.42(3H, s), 3.51(2H, s)

Specific rotation (sulfate): $[\alpha]_D^{22.5} = +71.0°$ (C=0.2, $H_2O$)

(EXAMPLE 28)

Synthesis of 2'-N-(3-hydroxybutyl) fortimicin A [the compound represented by general formula (I) wherein $R_0$=H and R=$CH_2CH_2CH(OH)CH_3$]
Yield: 260 mg 55%

Rf value in silica gel TLC (developer: lower layer of chloroform:methanol:28% aqueous ammonia=1:1:1): 0.69

Nuclear magnetic resonance spectrum (in $D_2O$) δ (in ppm): 0.96(3H, d), 1.04(3H, d), 3.03(3H, s), 3.42(3H, s), 3.51(2H, s), 4.98(1H, d)

Mass spectrum (m/e): 477(M+), 420, 358, 302, 292, 274, 246, 215, 207, 169, 142, 115

Specific rotation: $[\alpha]_D^{22.5} = +55.5°$ (C=0.2, $H_2O$)

(EXAMPLE 29)

Synthesis of 2'-N-benzyl fortimicin A [the compound represented by general formula (I) wherein $R_0$=H and R=$CH_2C_6H_5$]
Yield: 110 mg 22.4%

Rf value in silica gel TLC (developer: lower layer of chloroform:methanol:28% aqueous ammonia=1:1:1): 0.81

Nuclear magnetic resonance spectrum (in $D_2O$) δ (in ppm): 1.04(3H, d), 3.03(3H, s), 3.42(3H, s), 3.45(2H, s), 3.80(2H, s), 5.01(1H, d), 7.32(5H, s)

Specific rotation: $[\alpha]_D^{22.5} = +75.0°$ (C=0.2, $H_2O$)

(EXAMPLE 30)

Synthesis of 2'-N-(3-phenylpropyl)fortimicin A [the compound represented by general formula (I) wherein $R_0$=H and

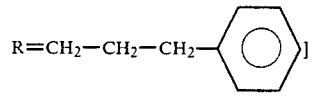

Yield: 320 mg 65%

Rf value in silica gel TLC (developer: lower layer of chloroform:methanol:28% aqueous ammonia=1:1:1): 0.84

Nuclear magnetic resonance spectrum (in $D_2O$) δ (in ppm): 1.05(3H, d), 3.01(3H, s), 3.43(3H, s), 3.42(2H, s), 4.90(1H, d), 7.30(5H, s)

Specific rotation (sulfate): $[\alpha]_D^{22.5} = +42.5°$ (C=0.2, $H_2O$)

EXAMPLE 31

Synthesis of 2'-N-methyl fortimicin A [the compound represented by general formula (I) wherein $R_0$=H and R=$CH_3$]

1.1 g of 2'-N-methyl fortimicin B obtained in Example 9 is dissolved in 50 ml of methanol. To the solution is added 2.4 g (3.3 moles per mole of the starting compound) of benzyloxycarbonyloxysuccinimide at room temperature and the mixture is allowed to react for 18 hours. After the reaction mixture is concentrated, 50 ml of ethyl acetate is added to the residue and the water-soluble material is extracted with 50 ml of water and removed. Then, the separated ethyl acetate layer is dried over anhydrous sodium sulfate and the solvent is removed by distillation to obtain a residue containing the desired compound wherein the amino groups other than that at the 4-position of 2'-N-methyl fortimicin B are protected. The obtained residue is dissolved in 40 ml of tetrahydrofuran and then mixed with the solution of 1-hydroxybenzotriazole ester of N-benzyloxycarbonylglycin prepared in the following manner. That is, 480 mg of N-benzyloxyglycin and 310 mg of 1-hydroxybenzotriazole are dissolved in 70 ml of tetrahydrofuran; 470 mg of dicyclohexylcarbodiimide is added to the solution under ice cooling and the mixture is stirred for 3 hours keeping the same temperature; the precipitated crystals are filtered off and then washed with 10 ml of tetrahydrofuran. The resulting filtrate is added to the above-mentioned tetrahydrofuran solution and the mixture is allowed to react at room temperature for 24 hours. After the reaction mixture is concentrated, 60 ml of 0.2 N-HCl methanol and 200 mg of palladium carbon catalyst are added to the residue and reductive hydrogenolysis is carried out by passing hydrogen gas at room temperature and at atmospheric pressure for 3 hours. The catalyst is removed from the reaction mixture by filtration and the filtrate is concentrated. To the residue is added 60 ml of water and the resulting solution is adjusted to pH 5.5 with 1 N NaOH. Then, the solution is passed through a column (2 cm in inside diameter) packed with 100 ml of Amberlite CG-50 ($NH_4^+$ form). After the column is washed with 500 ml of water, elution is carried out with 0.2 N aqueous ammonia and the eluate is taken in 20 ml fractions. Fraction Nos. 35–48 are combined and the aqueous ammonia is removed therefrom by distillation to obtain 430 mg of a white powder. The powder has the following properties and is identified as 2'-N-methyl fortimicin A. Yield: 33.8%

EXAMPLE 31

The properties of the obtained powder are as follows.
Rf value in silica gel TLC (developer: lower layer of chloroform:methanol:28% aqueous ammonia=1:1:1): 0.69

Nuclear magnetic resonance spectrum (in $D_2O$) δ (in ppm): 1.03(3H, d), 2.33(3H, s), 3.06(3H, s), 3.44(3H, s), 3.52(2H, d), 5.00(1H, d)

Specific rotation (sulfate): $[\alpha]_D^{23} = +78.5°$ (C=0.2, $H_2O$)

Mass spectrum (m/e): 419(M+), 362, 292, 274, 235, 207, 197, 173, 157, 57

EXAMPLE 32

Synthesis of 2'-N-[(R,S)-3-amino-2-hydroxypropionyl]fortimicin A [the compound represented by general formula (I) wherein $R_0$=H and

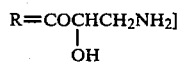

200 mg (0.84 mmole) of R,S-3-benzyloxycarbonylamino-2-hydroxypropionic acid and 98 mg of N-hydroxysuccinimide are dissolved in 8 ml of tetrahydrofuran. To the solution is added 180 mg of N,N'-dicyclohexylcarbodiimide under ice cooling and the mixture is stirred for one hour. The precipitated crystals are removed from the reaction mixture by filtration. The filtrate is mixed with 500 mg of 1,6'-di-N-benzyloxycarbonyl-4-N-(N-benzyloxycarbonylglycyl)fortimicin B obtained in Example 12 and reaction is carried out at room temperature for 6 hours. After the reaction mixture is concentrated, 15 ml of 0.2 N-HCl methanol and 50 mg of palladium carbon catalyst are added to the residue and reductive hydrogenolysis is carried out by passing hydrogen gas for 3 hours. Then, the catalyst is filtered off and the filtrate is concentrated. To the residue is added 15 ml of water and the resulting solution is adjusted to pH 6 with 1 N NaOH. The solution is then passed through a column (0.8 cm in inside diameter) packed with 30 ml of Amberlite CG-50 ($NH_4^+$ form). After the column is washed with 150 ml of water, elution is carried out with 0.2 N aqueous ammonia and the eluate is taken in 15 ml fractions. Fraction Nos. 12–16 are combined and the aqueous ammonia is removed therefrom by distillation to obtain 260 mg of a white powder. The powder has the following properties and is identified as the above-mentioned compound. Yield: 86%

Rf value in silica gel TLC (developer: lower layer of chloroform:methanol:28% aqueous ammonia=1:1:1): 0.56, 0.51 (R-form and S-form of this compound are separated on the silica gel plate)

Nuclear magnetic resonance spectrum (in $D_2O$) δ (in ppm): 1.01(3H, d), 2.7–3.1(4H, m), 3.06 (3H, s), 3.44(3H, s), 3.5(2H, s), 4.87(1H, d)

Specific rotation (sulfate): $[\alpha]_D^{21} = +90.5°$ (C=0.2, $H_2O$)

Mass spectrum (m/e): 492(M+), 444, 349, 246, 235, 230, 207, 154

EXAMPLE 33

Synthesis of 2'-N-[(R,S)-3-N-benzyloxycarbonylamino-2-hydroxypropionyl] fortimicin B [the compound represented by general formula (II) wherein

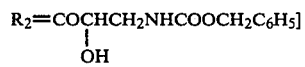

3.30 g of R,S-3-benzyloxycarbonylamino-2-hydroxypropionic acid and 1.58 g of N-hydroxysuccinimide are dissolved in 50 ml of tetrahydrofuran. To the solution is added 2.84 g of dicyclohexylcarbodiimide under ice cooling and the mixture is allowed to react for one hour keeping the same temperature. The precipitated crystals are removed from the reaction mixture by filtration, whereby a tetrahydrofuran solution of N-hydroxysuccinimide ester of R,S-3-benzyloxycarbonylamino-2-hydroxypropionic acid is obtained. The solution is mixed with 50 ml of a methanol solution wherein 4.0 g of fortimicin B is dissolved and reaction is carried out at room temperature for 18 hours. After the reaction mixture is concentrated, 100 ml of water is added to the residue to extract the water-soluble part. The resulting solution is adjusted to pH 6 with 1 N HCl and then passed through a column (2.5 cm in inside diameter) packed with 100 ml of Amberlite CG-50 ($NH_4^+$ form). After the column is washed with 500 ml of water, elution is carried out with 0.075 N aqueous ammonia and the eluate is taken in 20 ml fractions. Fraction Nos. 56–84 are combined and the aqueous ammonia is removed therefrom by distillation to obtain 2.16 g of a white powder. The powder has the following properties and is identified as the above-mentioned compound. Yield: 33%

Rf value in silica gel TLC (developer: lower layer of chloroform:methanol:28% aqueous ammonia=1:1:1): 0.78

Nuclear magnetic resonance spectrum (in $D_2O$) δ (in ppm): 1.04(3H, d), 2.34(3H, s), 2.6–3.1 (5H, m), 3.44(3H, s), 5.12(2H, s), 7.33(5H, s)

EXAMPLE 34

Synthesis of 2'-N-[(R,S)-3-amino-2-hydroxypropyl]-fortimicin B [the compound represented by general formula (IV) wherein $R_0$=H and $$R_3 = CH_2-\underset{OH}{CH}-CH_2-NH_2]$$

680 mg (1.2 mmoles) of 2'-N-[(R,S)-3-N-benzyloxycarbonylamino-2-hydroxypropionyl]fortimicin B obtained in Example 33 is dissolved in 10 ml of tetrahydrofuran. To the solution is added 12 ml of a solution of diborane in tetrahydrofuran (1 mole solution of $BH_3$) and the mixture is allowed to react at room temperature for one hour. 0.4 ml of water is added to the reaction mixture and the excess diborane is decomposed. After the mixture is concentrated to dryness, 22 ml of 0.2 N-HCl methanol and 100 mg of 10% palladium carbon catalyst are added to the residue and hydrogenolysis is carried out by passing hydrogen gas at room temperature and at atmospheric pressure for 18 hours. The catalyst is removed from the reaction mixture by filtration and the filtrate is concentrated. To the residue is added 30 ml of water and the resulting solution is adjusted to pH 6 with 1 N NaOH. The solution is then passed through a column (1.5 cm in inside diameter) packed with 50 ml of Amberlite CG-50 ($NH_4^+$ form) to adsorb the product on the resin. After the column is washed with 300 ml of water, elution is carried out with 0.2 N aqueous ammonia and the eluate is taken in 15 ml fractions. Fraction Nos. 20–32 are combined and the aqueous ammonia is distilled away to obtain 300 mg of a white powder. The powder has the following properties and is identified as the above-mentioned compound. Yield: 59.4%

Rf value in silica gel TLC (developer: lower layer of chloroform:methanol:28% aqueous ammonia=1:1:1): 0.51, 0.46 (D-form and L-form of this compound are separated on the silica gel plate)

Nuclear magnetic resonance spectrum (in methanol-$d_4$) δ (in ppm): 1.08(3H, d), 7.34(3H, s), 2.6–3.2 (7H, m), 3.43(3H, s), 5.0(1H, d)

Mass spectrum (m/e): 422($M^+$+1), 403, 361, 332, 235, 216, 207, 142

EXAMPLE 35

Synthesis of 2'-N-[(R,S)-3-benzyloxycarbonylamino-2-hydroxypropyl-1,6'-di-N-benzyloxycarbonyl fortimicin B [the compound represented by general formula (III) wherein $$R_2 = CH_2-\underset{OH}{CH}-CH_2-NHCOOCH_2C_6H_5$$

and $R_4 = COOCH_2C_6H_5$]

400 mg (1.0 mmole) of 2'-N-[(R,S)-3-amino-2-hydroxypropyl]fortimicin B is dissolved in 20 ml of methanol. To the solution is added 820 mg (3.3 mmoles) of N-benzyloxycarbonyloxysuccinimide and the mixture is allowed to react to room temperature for 18 hours. The reaction mixture is concentrated and 5 ml of chloroform is added to the residue to extract the soluble part. The resulting chloroform solution is passed through a column (1.5 cm in inside diameter) packed with 25 g of a silica gel. Elution is carried out with chloroform-methanol (19:1) and the eluate is taken in 20 ml fractions. Fraction Nos. 16–28 are combined and the solvent is distilled away to obtain 140 mg of a white powder. The powder has the following properties and is identified as the above-mentioned compound. Yield: 70.2%

Rf value in silica gel TLC (developer: chloroform:methanol=17:3): 0.38

Nuclear magnetic resonance spectrum (in methanol-$d_4$) δ (in ppm): 1.04(3H, d), 2.38(3H, s), 2.4–3.1(3H, m), 3.46(3H, s), 5.06(6H, s), 7.34(15H, s)

EXAMPLE 36

Synthesis of 2'-N-[(R,S)-3-amino-2-hydroxypropyl]-fortimicin A [the compound represented by general formula (I) wherein $R_0$=H and $$R = CH_2-\underset{OH}{CH}-CH_2NH_2]$$

160 mg of N-benzyloxycarbonylglycin and 110 mg of 1-hydroxybenzotriazole are dissolved in 20 ml of tetrahydrofuran. To the solution is added 180 mg of N,N'-dicyclohexylcarbodiimide under ice cooling and the mixture is allowed to react at 0°–5° C. for one hour. The precipitated crystals are removed from the reaction mixture by filtration. To the filtrate is added 560 mg (0.7 mmole) of 2'-N-[(R,S)-3-benzyloxycarbonylamino-2-hydroxypropyl]-1,6'-di-N-benzyloxycarbonyl fortimicin B obtained in Example 35 and the mixture is allowed to react at room temperature for 18 hours. After the reaction mixture is concentrated to dryness, 20 ml of 0.2 N-HCl methanol and 70 mg of palladium carbon catalyst are added to the residue and reductive hydrogenolysis is carried out by passing hydrogen gas for 6 hours. The catalyst is removed from the mixture by filtration and the filtrate is concentrated. To the residue is added 20 ml of water and the resulting solution is adjusted to pH 6 with 1 N NaOH. The solution is then passed through a column (0.8 cm in inside diameter) packed with 30 ml of Amberlite CG-50 ($NH_4^+$ form). After the column is washed with 150 ml of water, elution is carried out with 0.4 N aqueous ammonia and the eluate is taken in 20 ml fractions. Fraction Nos. 19–32 are combined and the solvent is distilled away to obtain 180 mg of a white powder. The powder has the following properties and is identified as the above-mentioned compound. Yield: 54.3%

Rf value in silica gel TLC (developer is the same as in Example 21): 0.46

Nuclear magnetic resonance spectrum (in $D_2O$) δ (in ppm): 1.06(3H, d), 2.4–3.0(7H, m), 3.05 (3H, s), 3.44(3H, s), 3.53(2H, s), 5.05(1H, d)

Specific rotation (sulfate): $[\alpha]_D^{21} = +67.5°$ (C=0.2, $H_2O$)

Mass spectrum (m/e): 460($M^+$-$NH_3$), 403, 361, 258, 216, 207, 86

EXAMPLE 37

Synthesis of 2'-N-(2-hydroxyethyl) fortimicin A (Compound 14) (another method)

810 mg (2 mmoles) of 2'-N-glycolyl fortimicin B obtained in Example 5 is dissolved in 20 ml of tetrahydrofuran. To the solution is added 20 ml of a solution of diborane in tetrahydrofuran (1 mole solution of $BH_3$) and the mixture is allowed to react at room temperature for one hour. 0.5 ml of water is added to the reaction mixture and the unreacted diborane is decomposed. After the mixture is concentrated to dryness, 25 ml of 0.2 N-HCl methanol is added to the residue. The resulting solution is allowed to stand overnight and then adjusted to pH 10 with 1 N NaOH. To the solution is added 1.1 g (4.4 mmoles) of N-benzyloxycarbonyloxysuccinimide and the mixture is allowed to react at room temperature for 16 hours. Then, the reaction mixture is concentrated and 50 ml of ethyl acetate is added to the residue to extract the soluble part. After washing with 50 ml of water, the ethyl acetate layer is separated and concentrated to dryness. The obtained pale yellowish powder is dissolved in 20 ml of tetrahydrofuran. To the solution is added a filtrate which is obtained by reacting 420 mg of N-benzyloxycarbonylglycin with 270 mg of 1-hydroxybenzotriazole and 410 mg of N,N'-dicyclohexylcarbodiimide in 10 ml of tetrahydrofuran at 0° C. for one hour and removing the precipitate by filtration. The mixture is allowed to react at room temperature for 18 hours. After the reaction mixture is concentrated, 30 ml of 0.2 N-HCl methanol and 120 mg of palladium carbon catalyst are added to the residue and hydrogenolysis is carried out by passing hydrogen gas at room temperature and at atmospheric pressure for 3 hours. The catalyst is removed from the mixture by filtration and the filtrate is concentrated. To the residue is added 30 ml of water and the resulting solution is adjusted to pH 5.5 with 1 N NaOH. The solution is then passed through a column (1.5 cm in inside diameter) packed with 50 ml of Amberlite CG-50 ($NH_4^+$ form). After the column is washed with 500 ml of water, elution is carried out with 0.2 N aqueous ammonia and the eluate is taken in 15 ml fractions. Fraction Nos. 18–24 are combined and the aqueous ammonia is distilled away to obtain 280 mg of a white powder. The powder has the same properties as the powder obtained in Example 24 and is identified as 2'-N-(2-hydroxyethyl)fortimicin A. Yield: 31.2%

EXAMPLE 38

Synthesis of 2'-N-[(S)-4-amino-2-hydroxybutyl] fortimicin A (Compound 16) (another method)

870 mg (2 mmoles) of 2'-N-[(S)-4-amino-2-hydroxybutyl]fortimicin B obtained in Example 8 is dissolved in 40 ml of methanol. To the solution is added 1.6 g (6.6 mmoles) of N-benzyloxycarbonyloxysuccinimide and the mixture is allowed to react at room temperature for 6 hours. The reaction mixture is concentrated and 50 ml of chloroform is added to the residue to extract the soluble part. After washing with 50 ml of water, the chloroform layer is separated and dried over anhydrous sodium sulfate. The solvent is distilled away and the obtained pale yellowish powder is dissolved in 20 ml of tetrahydrofuran. To the solution is added a filtrate which is obtained by reacting 420 mg of N-benzyloxycarbonylglycin with 270 mg of 1-hydroxybenzotriazole and 410 mg of N,N'-dicyclohexylcarbodiimide in 10 ml of tetrahydrofuran at 0° C. for one hour and removing the precipitate by filtration. The mixture is allowed to react at room temperature for 24 hours. After the reaction mixture is concentrated, 30 ml of 0.2 N-HCl methanol and 140 mg of palladium carbon catalyst are added to the residue and hydrogenolysis is carried out by passing hydrogen gas at room temperature and at atmospheric pressure for 4 hours. The catalyst is removed from the mixture by filtration and the filtrate is concentrated. To the residue is added 30 ml of water and the resulting solution is adjusted to pH 5.5 with 1 N NaOH. The solution is then passed through a column (1.5 cm in inside diameter) packed with 50 ml of Amberlite CG-50 ($NH_4^+$ form). After the column is washed with 500 ml of water, elution is carried out with 0.5 N aqueous ammonia and the eluate is taken in 15 ml fractions. Fraction Nos. 26–38 are combined and the aqueous ammonia is distilled away to obtain 340 mg of a white powder. The powder has the same properties as the powder obtained in Example 23 and is identified as 2'-N-[(S)-4-amino-2-hydroxybutyl] fortimicin A. Yield: 34.5%

EXAMPLE 39

Synthesis of sulfate of 2'-N-i-propyl fortimicin A (The sulfates mentioned in the above examples are prepared according to this method.)

200 mg of free base of 2'-N-i-propyl fortimicin A obtained in Example 16 is dissolved in 0.5 ml of water and the solution is adjusted to pH 3 with 1 N sulfuric acid. Then, the solution is added dropwise to 100 ml of ethanol and the resulting precipitate is isolated by filtration. As the result, 260 mg of sulfate of 2'-N-i-propyl fortimicin A is obtained. Yield: 90.4%

Nuclear magnetic resonance spectrum (in $D_2O$) δ (in ppm): 1.34(6H, d), 1.41(3H, d), 3.12 (3H, s), 3.49(3H, s), 4.06(2H, s), 5.40(1H, d)

Elementary analysis: Calculated for $C_{20}H_{41}N_5O_6 \cdot 2H_2SO_4 \cdot C_2H_5OH \cdot 2H_2O$: C=34.23%, H=7.90%, N=9.98%. Found: C=34.50%, H=7.99%, N=9.71%.

What is claimed is:

1. 2'-N-substituted derivatives of fortimicin A, represented by the formula:

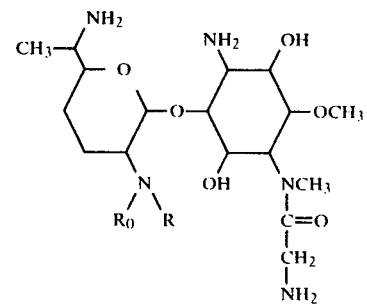

wherein $R_0$ represents a lower alkyl group having 1 to 4 carbon atoms and R represents a group represented by

or $-CHR_{11} R_{12}$ wherein $R_1$ is an alkyl group having 1 to 8 carbon atoms, aminoalkyl group having 2 to 8 carbon atoms, hydroxyalkyl group having 1 to 5 carbon atoms, N-alkylaminoalkyl group having 2 to 12 carbon atoms, aminohydroxyalkyl group having 2 to 8 carbon atoms and wherein the amino group and hydroxy group are bonded to different carbon atoms, or N-alkylaminohydroxyalkyl group having 2 to 8 carbon atoms and $R_{11}$ and $R_{12}$ may be the same or different and are a hydrogen atom, alkyl group having 1 to 8 carbon atoms, aminoalkyl group having 1 to 8 carbon atoms, hydroxyalkyl group having 1 to 5 carbon atoms, carbamoylaminoalkyl group having 2 to 9 carbon atoms, N-alkylaminoalkyl group having 2 to 12 carbon atoms, aminohydroxylalkyl group having 2 to 8 carbon atoms and wherein the amino group and hydroxy group are bonded to different carbon atoms, arylalkyl group having 7 to 12 carbon atoms, N-alkylaminohydroxyalkyl group having 2 to 8 carbon atoms or aryloxyalkyl group having 7 to 12 carbon atoms or $R_{11}$ and $R_{12}$ form a cyclohexyl group and the pharmaceutically acceptable acid addition salts thereof.

2. 2'-N-substituted derivatives of fortimicin A according to claim 1, wherein the derivatives are represented by the formula:

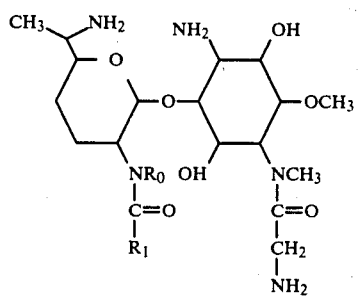

wherein $R_0$ and $R_1$ have the same significance as defined in claim 1 and the pharmaceutically acceptable non-toxic acid addition salts thereof.

3. 2'-N-substituted derivatives of fortimicin A according to claim 1, wherein the derivatives are represented by the formula:

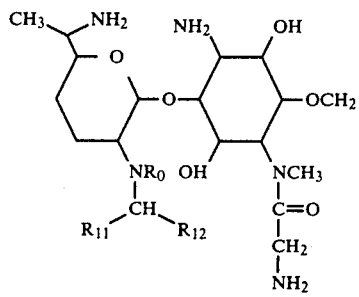

wherein $R_0$, $R_{11}$ and $R_{12}$ have the same significance as defined in claim 1 and the pharmaceutically acceptable non-toxic acid addition salts thereof.

* * * * *